(12) United States Patent
Prado et al.

(10) Patent No.: US 8,519,708 B2
(45) Date of Patent: Aug. 27, 2013

(54) SMALL MAGNET AND RF COIL FOR MAGNETIC RESONANCE RELAXOMETRY

(75) Inventors: Pablo J. Prado, Boston, MA (US); Thomas J. Lowery, Jr., Belmont, MA (US)

(73) Assignee: T2 Biosystems, Inc., Lexington, MA (US)

( * ) Notice: Subject to any disclaimer, the term of this patent is extended or adjusted under 35 U.S.C. 154(b) by 478 days.

(21) Appl. No.: 12/741,789

(22) PCT Filed: Nov. 6, 2008

(86) PCT No.: PCT/US2008/012592
§ 371 (c)(1),
(2), (4) Date: Aug. 20, 2010

(87) PCT Pub. No.: WO2009/061481
PCT Pub. Date: May 14, 2009

(65) Prior Publication Data
US 2010/0308822 A1   Dec. 9, 2010

Related U.S. Application Data

(60) Provisional application No. 61/002,022, filed on Nov. 6, 2007, provisional application No. 61/008,991, filed on Dec. 21, 2007.

(51) Int. Cl.
*G01V 3/00*   (2006.01)

(52) U.S. Cl.
USPC ........................................................ 324/309

(58) Field of Classification Search
USPC ................................. 324/307–315, 318–322
See application file for complete search history.

(56) References Cited

U.S. PATENT DOCUMENTS

| | | | |
|---|---|---|---|
| 4,101,435 A | 7/1978 | Hasegawa et al. | |
| 4,452,773 A | 6/1984 | Molday | |
| 4,574,240 A | 3/1986 | Libove et al. | |
| 4,638,253 A * | 1/1987 | Jaskolski et al. | 324/311 |
| 4,875,486 A | 10/1989 | Rapoport et al. | |
| 4,920,061 A | 4/1990 | Poynton et al. | |
| 5,023,551 A * | 6/1991 | Kleinberg et al. | 324/303 |
| 5,049,819 A | 9/1991 | Dechene et al. | |

(Continued)

FOREIGN PATENT DOCUMENTS

| WO | WO-90/06045 A2 | 6/1990 |
|---|---|---|
| WO | WO-91/17428 A1 | 11/1991 |

(Continued)

OTHER PUBLICATIONS

Raich, et al., Design and Construction of a Dipolar Halbach Array with a Homogeneous Field from Identical Bar Magnets: NMR Mandhalas, Concepts in Magnetic Resonance Part B (Magnetic Resonance Engineering), vol. 23B(1), pp. 16-25, 2004.*

(Continued)

*Primary Examiner* — Melissa Koval
*Assistant Examiner* — Daniel Miller
(74) *Attorney, Agent, or Firm* — Clark & Elbing LLP

(57) ABSTRACT

Small and inexpensive probeheads for use in nuclear magnetic resonance systems, in particular, magnetic resonance relaxometry systems are provided. The design of the magnet-radiofrequency coil configurations within the probeheads is guided by an excitation bandwidth associated with radiofrequency pulses to be applied to a sample.

14 Claims, 11 Drawing Sheets

(56) References Cited

U.S. PATENT DOCUMENTS

| | | | |
|---|---|---|---|
| 5,136,095 | A | 8/1992 | Tarnowski et al. |
| 5,164,297 | A | 11/1992 | Josephson et al. |
| 5,204,457 | A | 4/1993 | Maruno et al. |
| 5,254,460 | A | 10/1993 | Josephson et al. |
| 5,262,176 | A | 11/1993 | Palmacci et al. |
| 5,424,419 | A | 6/1995 | Hasegawa et al. |
| 5,445,970 | A | 8/1995 | Rohr |
| 5,445,971 | A | 8/1995 | Rohr |
| 5,492,814 | A | 2/1996 | Weissleder |
| 5,572,132 | A | 11/1996 | Pulyer et al. |
| 5,637,469 | A | 6/1997 | Wilding et al. |
| 5,801,003 | A | 9/1998 | Shimamura et al. |
| 5,910,728 | A | 6/1999 | Sodickson |
| 6,013,188 | A | 1/2000 | Terstappen et al. |
| 6,097,188 | A | 8/2000 | Sweedler et al. |
| 6,165,378 | A | 12/2000 | Maruno et al. |
| 6,194,898 | B1 | 2/2001 | Magnuson et al. |
| 6,194,900 | B1 | 2/2001 | Freeman et al. |
| 6,294,342 | B1 | 9/2001 | Rohr et al. |
| 6,297,062 | B1 | 10/2001 | Gombinski |
| 6,342,396 | B1 | 1/2002 | Perrin et al. |
| 6,361,944 | B1 | 3/2002 | Mirkin et al. |
| 6,456,072 | B1 | 9/2002 | Webb et al. |
| 6,489,767 | B1 * | 12/2002 | Prado et al. ............... 324/318 |
| 6,500,343 | B2 | 12/2002 | Siddiqi |
| 6,548,311 | B1 | 4/2003 | Knoll |
| 6,599,498 | B1 | 7/2003 | Groman et al. |
| 6,630,355 | B1 | 10/2003 | Pivarnik et al. |
| 6,767,635 | B1 | 7/2004 | Bahr et al. |
| 6,788,061 | B1 | 9/2004 | Sweedler et al. |
| 6,822,454 | B2 | 11/2004 | Peck et al. |
| 6,866,838 | B1 | 3/2005 | Mondain-Monval et al. |
| 6,884,357 | B2 | 4/2005 | Siddiqi |
| 6,940,378 | B2 | 9/2005 | Miller et al. |
| 6,958,609 | B2 | 10/2005 | Raftery et al. |
| 7,001,589 | B2 | 2/2006 | Mondain-Monval et al. |
| 7,018,849 | B2 | 3/2006 | Piasio et al. |
| 7,034,536 | B2 | 4/2006 | Higuchi |
| 7,141,978 | B2 | 11/2006 | Peck et al. |
| 7,200,430 | B2 | 4/2007 | Thomas et al. |
| 7,217,457 | B2 | 5/2007 | Elaissari et al. |
| 7,217,542 | B2 | 5/2007 | Tyvoll et al. |
| 7,332,353 | B2 | 2/2008 | Baudry et al. |
| 7,345,479 | B2 | 3/2008 | Park et al. |
| 7,459,145 | B2 | 12/2008 | Bao et al. |
| 7,517,457 | B2 | 4/2009 | Siddiqi |
| 7,553,542 | B2 | 6/2009 | Ou et al. |
| 7,560,923 | B2 | 7/2009 | Viswanathan |
| 7,564,245 | B2 | 7/2009 | Lee |
| 7,781,228 | B2 | 8/2010 | Menon et al. |
| 7,829,350 | B2 | 11/2010 | Josephson et al. |
| 2003/0216638 | A1 | 11/2003 | Dharmakumar et al. |
| 2003/0222648 | A1 | 12/2003 | Fan |
| 2004/0018611 | A1 | 1/2004 | Ward et al. |
| 2007/0166730 | A1 | 7/2007 | Menon et al. |
| 2008/0204022 | A1 | 8/2008 | Sillerud et al. |
| 2008/0305048 | A1 | 12/2008 | Josephson et al. |
| 2009/0099342 | A1 | 4/2009 | Braconnot et al. |
| 2010/0072994 | A1 | 3/2010 | Lee et al. |
| 2010/0120174 | A1 | 5/2010 | Josephson et al. |

FOREIGN PATENT DOCUMENTS

| | | |
|---|---|---|
| WO | WO-98/04740 A1 | 2/1998 |
| WO | WO-01/00876 A1 | 1/2001 |
| WO | WO-01/11360 A2 | 2/2001 |
| WO | WO-01/19405 A2 | 3/2001 |
| WO | WO-02/074164 A1 | 9/2002 |
| WO | WO-02/098364 A2 | 12/2002 |
| WO | WO-2005/061724 A1 | 7/2005 |
| WO | WO-2005/099419 A2 | 10/2005 |
| WO | WO-2005/111596 A1 | 11/2005 |
| WO | WO-2006/122083 A2 | 11/2006 |
| WO | WO-2007/106765 A2 | 9/2007 |
| WO | WO-2008/007270 A2 | 1/2008 |
| WO | WO-2008/010111 A2 | 1/2008 |
| WO | WO-2008/072156 A2 | 6/2008 |
| WO | WO-2008/119054 A1 | 10/2008 |
| WO | WO-2008/137721 A2 | 11/2008 |
| WO | WO-2009/017697 A2 | 2/2009 |
| WO | WO-2009/026251 A1 | 2/2009 |
| WO | WO-2009/045354 A1 | 4/2009 |
| WO | WO-2009/085214 A1 | 7/2009 |
| WO | WO-2010/002479 A1 | 1/2010 |
| WO | WO-2010/051362 A1 | 5/2010 |

OTHER PUBLICATIONS

Demas, et al., Portable, low-cost NMR with laser-lathe lithography produced microcoils, J. Mag. Reson. 189 (2007), pp. 121-129, available online Aug. 23, 2007.*

Demas, et al., Electronic characterization of lithographically patterned microcoils for high sensitivity NMR detection, J. Mag. Reson. 200 (2009), pp. 56-63, available online Jun. 9, 2009.*

Rogers, et al., Using microcontact printing to fabricate microcoils on capillaries for high resolution proton nuclear magnetic resonance on nanoliter volumes, Appl. Phys. Lett. 70 (18), May 5, 1997.*

Baumgartner et al., Investigation of the State and Dynamics of Water in Hydrogels of Cellulose Ethers by 1H NMR Spectroscopy, AAPS PharmSciTech, 3(4) article 36, 2002.*

Atanasijevic et al., "Calcium-sensitive MRI contrast agents based on superparamagnetic iron oxide nanoparticles and calmodulin", *PNAS* 130(40):14707-14712 (2006).

Baudry et al., "Acceleration of the recognition rate between grafted ligands and receptors with magnetic forces" *PNAS* 103:16076-16078 (2006).

Bilgen et al., "In vivo magnetic resonance microscopy of rat spinal cord at 7 T using implantable RF coils", *Magnetic Resonance in Medicine* 46:1250-1253 (2001).

Cohen-Tannoudji et al. "Measuring the kinetics of biomolecular recognition with magnetic colloids", *Physical Review Letters*, 100:108301-1-10301-4 (2008).

Costanzo et al., "Protein-ligand mediated aggregation of nanoparticles: a study of synthesis and assembly mechanism", *Chem. Mater.* 16:1775-1785 (2004).

Daniel et al., "Implantable diagnostic device for cancer monitoring", *Biosensors and Bioelectronics* 24(11):3252-3257 (2009).

Decorps et al., "An inductively coupled, series tunes NMR probe", *J. Magnetic Resonance* 65: 100-109(1985).

Demas et al., "Portable, low-cost NMR with laser-lathe lithography produced microcoils", *J. Magnetic Resonance* 189:121-129 (2007).

Dreyfus et al., "Microscopic artificial swimmers", *Nature* 437:862-865 (2005).

Elgort et al., "A review of technical advances in interventional magnetic resonance imaging" *Academic Radiology* 12(9): 1089-1099 (2005).

Fry et al., "A new approach to template purification for sequencing applications using paramagnetic particles", *BioTechniques* 13(1):124-131, (1992).

Gijs, "Magnetic bead handling on-chip: new opportunities for analytical applications", *Microfluid Nanofluid* 1:22-40 (2004).

Gilderdale et al., "An inductively-coupled, detachable receiver coil system for use with magnetic resonance compatible endoscopes", *J. Magnetic Resonance Imaging* 18:131-135 (2003).

Grimm, "Novel nanosensors for rapid analysis of telomerase activity" *Cancer Research* 64:639-643 (2004).

Hong et al. "Magnetic microparticle aggregation for viscosity determination by MR", *Magnetic Resonance in Medicine* 59:515-520 (2008).

Josephson et al., "Magnetic nanosensors for the detection of oligonucleotide sequences", *Angew Chem* 40(17):3204-3206 (2001).

Josephson et al., "High-efficiency intracellular magnetic labeling with novel superparamagnetic-TAT peptide conjugates", *Bioconjugate Chem.* 10(2) pp. 186-191 (1999).

Kim et al., "Magnetic relaxation switch detection of human chorionic gonadotropin", *Bioconjugate Chemistry* 18(6):2024-2028 (2007).

Koh et al. "Sensitive NMR sensors detect antibodies to influenza", *Angew Chem.Int. Ed. Engl.* 47:4119-4121 (2008).

Kotitz et al., "Determination of the binding reaction between avidin and biotin by relaxation measurements of magnetic nanoparticles", *Journal of Magnetism and Magnetic Materials* 194:62-68 (1999).

Kriz et al., "Magentic permeability measurements in bioanalysis and biosensors", *Anal. Chem.* 68:1966-1970 (1996).

Kriz et al., "Advancements toward magneto immunoassays", *Biosensors and Bioelectronics* 13:817-823 (1998).

Lee et al., "Microelectromagnets for the control of magnetic nanoparticles", *Appl. Phys. Letters* 79:3308-3310 (2001).

Lee et al., "Ligand-receptor interactions in chains of colloids: when reactions are limited by rotational diffusion", *Langmuir* 24:1296-1307 (2008).

Lewin et al., "TAT peptide-derivatised magneitc nanoparticles allow in vivo tracking and revcovery of progenitor cells", *Nature Biotechnology* 18:410-414 (2000).

Magin et al., "Miniature magnetic resonance machines", *IEEE Spectrum* 34(10):51-61 (1997).

Makiranta et al., "Modeling and simulation of magnetic nanoparticle sensor", Proceedings of the 2005 IEEE, Shanghai, China, Sep. 1-4, 2005, 1256-1259 (2005).

Melba et al., "Laser-lathe lithography—a novel method for manufacturing nuclear magnetic resonance microcoils", *Biomedical Microdevices* 5(1):21-27 (2003).

Martin et al., "Strong intrinsic mixing in vortex magnetic fields", *Physical Review* 80:016312(1-6) (2009).

Martin, "Theory of strong intrinsic mixing of particle suspensions in vortex magnetic fields", *Physical Review* 79:011503(1-11) (2009).

Massin et al., "Planar micricoil-based microfluidic NMR probes" *J. Mag. Resonance* 164:242-255 (2003).

Massin et al., "Planar microcoil-based magnetic resonance imaging of cells", Transducers, Solid-state Sensors, Actuators and Microsystems 12th Int'l conference 2(9):967-970 (2003).

McDowell et al., "Operating nanoliter scale NMR microcoils in a 1 tesla field", *J. Mag. Resonance* 188:74-82 (2007).

Moser et al., "On-chip immune-agglutination assay with analyte capture by dynamic manipulation of superparamagnetic beads", *Lab Chip* 9:3261-3267 (2009).

Niemeyer et al., "Self-aasembly of DNA-strepavidiv nanostructrues and their use ias reagents in Immuno-PCR", *Nucleic Acid Research* 27(23):4553-4561 (1999).

Ogawa et al., "Development of a local NMR sensor for wetness monitoring of polymer electrolyte membrane using a planar surface coil", Kai National Heat Transfer Symposium of Japan Koen Ronbunshu, C114:99-100 (2005).

Olson et al., "High-resolution microcoil 1H-NMR for mass-limited, nanoliter-volumes samples", *Science* 270:1967-1970 (1995).

Peck et al., "RF microcoils patterned using microlithographic techniques for use as microsensors in NMR", Engineering in Medicine and Biology Society, Proceedings of the 15th annual international conference of the IEEE, Oct. 28-31, 1993, 174-175 (1993).

Perez et al., "DNA-based magnetic nanoparticle assembly acts as a magnetic relaxation nanoswitch allowing of DNA-cleaving agents", *J. Am. Chem. Soc.* 124(12):2856-2857 (2002).

Perez et al., "Magnetic relaxation switches capable of sensing molecular interactions", *Nature Biotechnology* 20:816-820 (2002).

Perez et al., "Viral-induced self assembly of magnetic nanoparticles allows the detection of viral particles in biological media", *J. Am. Chem. Soc.* 125:10192-10193 (2003).

Perez et al., "Use of magnetic nanoparticles as nanosensors to probe for molecular interactions", *ChemBioChem* 5:261-264 (2004).

Renaud et al., "Implantable planar rf microcoils for NMR microspectroscopy", *Sensors and Actuators A* 99:244-248 (2002).

Rida et al., "Long range transport of magnetic microbeads using simple planar coils placed in a uniform magnetostatic field" *Appl. Phys. Lett.* 83(12):2396-2398 (2003).

Routley et al., "The HALO system—a light weight portable imaging system", *Magentic Resonance Imaging* 22(8):1145-1151 (2004).

Shapiro et al., "Dynamic imaging with MRI contrast agents: quantitative considerations", *Magnetic Resonance Imaging* 24:449-462 (2006).

Sillerud et al., "1H NMR detection of superparamagnetic nanoparticles at 1 T using a microcoil and novel tuning circuit", *J. Mag. Resonance* 181:181-190 (2006).

Sun et al., "Experimental study on T2 relaxation time or protons in water suspensions of iron-oxide nanoparticles: waiting time dependence", *J. of Magnetism and Magnetic Materials* 321:2971-2975 (2009).

Syms et al., "MEMS Helmholtz coils for magnetic resonance imaging" *J. Micromech. Microeng.* 15:S1-S9 (2005).

Tong et al., "Coating optimization of superparamagnetic iron oxide nanoparticles for high T2 relaxivity"; *Nano Letters* 10(11):4607-4613 (2010).

Tsourkas et al., "Magnetic relaxation switch immunosensors detect enantiomeric impurities", *Angew Chem.* 43:2395-2399 (2004).

Webb and Grant, "Signal-to-noise and magnetic susceptibility trade-offs in solenoidal microcoils for NMR", *J. Mag. Resonance Series B* 113:83-87 (1996).

Weissleder et al., "Cell-specific targeting of nanoparticles by multivalent attachment of small molecules", *Nature Biotechnology* 23(11):1418-1423 (2005).

Wensink et al., "High signal to noise ratio in low field NMR on chip simulations and experimental results", Micro Electro Mechanical Systems 17th IEEE International Conference, Netherlands, 407-410 (2004).

Wirth et al., "A comparison of an inductively coupled implanted coil with optimized surface coils for in vivo NMR imaging of the spinal cord", *Magnetic Resonance in Medicine* 30:626-633 (1993).

Wu et al., "1H-NMR spectroscopy on the nanoliter scale for static and on-line measurements", *Anal. Chem.* 66:3849-3857 (1994).

Zhang et al., "A probe design for the acquisition of homonuclear, heteronuclear, and inverse detected NMR spectra from multiple samples", *J. Mag. Resonance* 153:254-258 (2001).

Extended European Search Report for European Application No. 08848455.5, dated Apr. 19, 2011 (8 pages).

International Preliminary Report on Patentability for International Application No. PCT/US2008/012592, dated May 11, 2010 (12 pages).

\* cited by examiner

SMALL MAGNET AND RF COIL FOR MAGNETIC RESONANCE RELAXOMETRY

CROSS REFERENCE TO RELATED APPLICATIONS

This application is the U.S. National Stage of International Application No. PCT/US2008/012592, filed Nov. 6, 2008 which claims the benefit of U.S. Provisional Application Nos. 61/002,022, filed Nov. 6, 2007 and 61/008,991, filed Dec. 21, 2007, all hereby incorporated by reference.

BACKGROUND OF THE INVENTION

Nuclear magnetic resonance (NMR) systems make use of nuclear magnetic resonance of atomic nuclei contained in a sample and are known to be able to provide a large variety of information characterizing the sample and corresponding sample components. Systems include, for example, magnetic resonance imaging (MRI) devices, magnet resonance spectrometers and magnetic resonance relaxometers. The nature of the nuclear magnetic resonance phenomenon requires the presence of a magnetic field upon excitation with a radiofrequency electromagnetic wave. Thus, generally, NMR systems include a magnet and a radiofrequency coil, either as separate system components or combined in a probehead.

Magnets that are preferred in magnetic resonance systems provide magnetic fields with high magnetic field strength and high homogeneity. Magnets known to satisfy these requirements are typically large and/or expensive. They are therefore not suitable for portable devices and/or implantation devices, and/or not suitable as part of disposable probeheads. Thus, a need exists for small, inexpensive probeheads for use in magnetic resonance systems, allowing portability, implantation and/or one-time use applications.

SUMMARY OF THE INVENTION

Provided probeheads and methods of preparing the same solve the problems of the current MR systems relating to portability, potential implantation and/or disposability of probeheads for use in MR systems. Probeheads provided in the present invention are particularly suitable, though not limited to, magnetic resonance relaxation measurements.

One embodiment is a small probehead for use in a magnetic resonance relaxometer. The probehead comprises (a) at least one magnet or magnetic field generator providing a magnetic field, (b) a space capable of accommodating a sample volume having an associated excitable volume, and (c) a radiofrequency coil having an associated detection volume, the radiofrequency coil being adapted and positioned such that its detection volume overlaps at least partly with an excitable volume. The provided magnetic field is inhomogeneous, and the space accommodating the sample volume and the radiofrequency coil are adapted and positioned according to a radiofrequency pulse optimized for the magnetic field distribution corresponding to the position of the sample volume. A provided probehead is optimized to obtain relaxometry parameters from a sample contained in the detection volume.

Another embodiment of is a probehead for magnetic resonance relaxometry. A small probehead comprises (a) two magnets or two magnetic field generators attached to a yoke, the south pole surface of one of the magnets or magnetic field generators opposing the north pole surface of the other magnet or magnetic field generator to form a gap between the magnets or magnetic field generators and to provide a magnetic field in the gap, (b) a space capable of accommodating a sample volume having an associated excitable volume, and (c) a radiofrequency coil within the gap, the radiofrequency coil having an associated detection volume and being adapted to emit a radiofrequency pulse with a pulse length, the radiofrequency coil being positioned and designed to have the detection volume partly overlap with an excitable volume within the gap. The provided magnetic field is inhomogeneous. Additionally, the space accommodating the sample volume and the radiofrequency coil are adapted and positioned according to a radiofrequency pulse bandwidth optimized for the magnetic field distribution corresponding to the position of the sample volume. The probehead is thus optimized to obtain relaxometry parameters from a sample contained in the sample volume.

Additionally provided are methods for preparing probeheads for use in a magnetic resonance relaxometry. In one embodiment is a method for preparing a probehead for use in a magnetic resonance relaxometer. The method comprises the steps of (a) providing at least one magnet or magnetic field generator providing a magnetic field, (b) providing a radiofrequency coil, (c) positioning the radiofrequency coil to have its associated detection volume overlap at least partly with an excitable volume, (d) positioning a space capable of accommodating a sample volume having an associated excitable volume; and (e) adapting the space for the sample volume and the radiofrequency coil according to a radiofrequency pulse optimized for the magnetic field distribution corresponding to the position of the detection volume. The probehead is thus optimized to obtain relaxometry parameters from a sample contained in the sample volume.

A further embodiment is a method of preparing a small probehead for use in portable magnetic resonance relaxometry. The method comprises the steps of (a) attaching two magnets or two magnetic field generators to a yoke such that the south pole surface of one of the magnets or magnetic field generators opposes the north pole surface of the other magnet or magnetic field generator to form a gap between the magnets or magnetic field generators and to provide a magnetic field in the gap, (b) positioning a space capable of accommodating a sample volume having an associated excitable volume, and (c) positioning a radiofrequency coil within the gap, the radiofrequency coil having an associated detection volume and being adapted to emit a radiofrequency pulse with a pulse length, the radiofrequency coil being positioned and designed to have the detection volume at least partly overlap with an excitable volume within the gap. The probehead is thus optimized to obtain relaxometry parameters from a sample contained in the sample volume.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF CERTAIN EMBODIMENTS OF THE INVENTION

Probeheads of the present invention include a magnet and/or magnetic field generator and at least one radiofrequency coil, and are much smaller and much less expensive than conventional combinations of magnet(s) and radiofrequency coil(s).

Weight and size of a probehead are critical factors for portable MR instruments. For example, weight and size reduction has implications in regards to system development and manufacturing, cost, and placement. Small probes may be, e.g., implantable in-vivo devices, embedded sensors for material testing, and sensors for on-line process monitoring. Additionally, because they are inexpensive provided small probeheads may be used in applications that benefit from disposable probeheads.

One aspect of the present invention is the scalability of a Magnetic Resonance (MR) probehead comprising a magnet and a radio-frequency (RF) coil. In particular, the present invention addresses the issue of significantly reducing size of probehead components while allowing measurement of magnetic resonance signal level(s), and, in particular, magnetic resonance relaxation parameter(s) and time(s). Designing a probehead specifically for relaxometry instead of conventional MR spectroscopy, allows for a dramatic reduction in its size and cost.

Magnet configuration and yoke design, if desired, can be accomplished initially by a theoretical prediction of what magnet and yoke configuration will lead to in terms of magnetic field strength. Suitable magnetic field strength will be discussed below. This can be done using standard analytical methods known in the art.

In one embodiment at least one magnet or magnetic field generator is shaped and/or configured to provide the magnetic field in a gap. In certain embodiments, a radiofrequency coil is positioned, either partly or completely within the gap of such a configuration.

Figure 1:
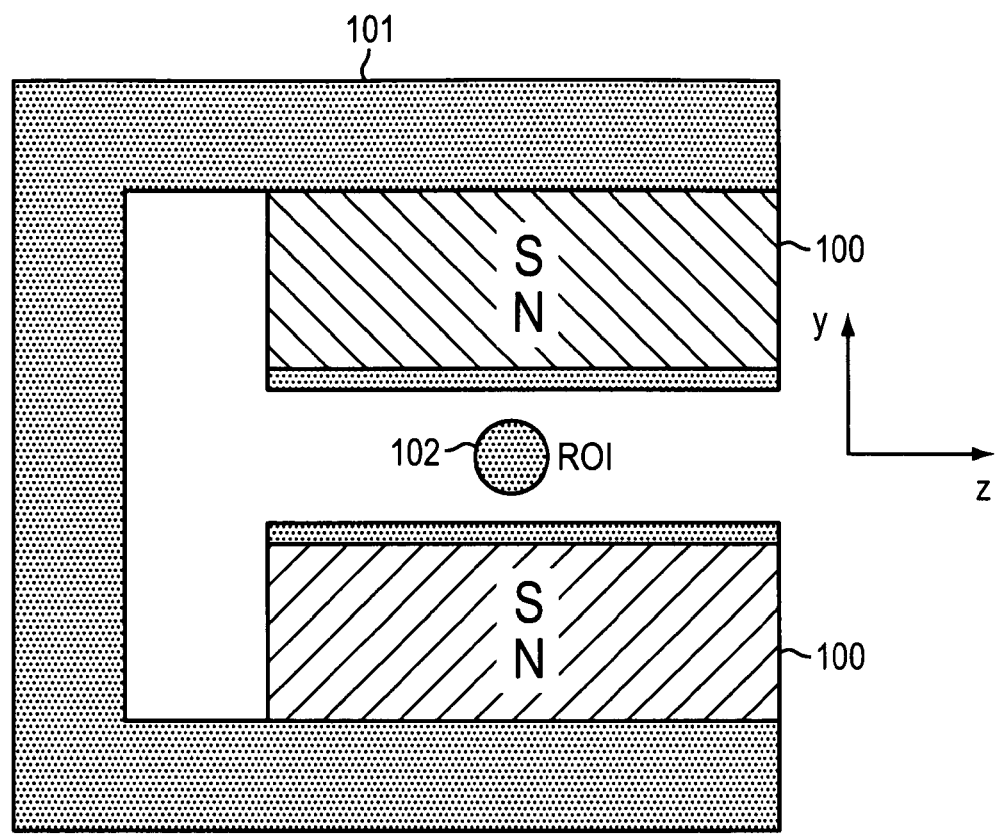
FIG. 1 provides a schematic representation of a probehead including a c-shaped yoke with magnets attached thereto and a radiofrequency coil placed between the magnets.
Figure 2:
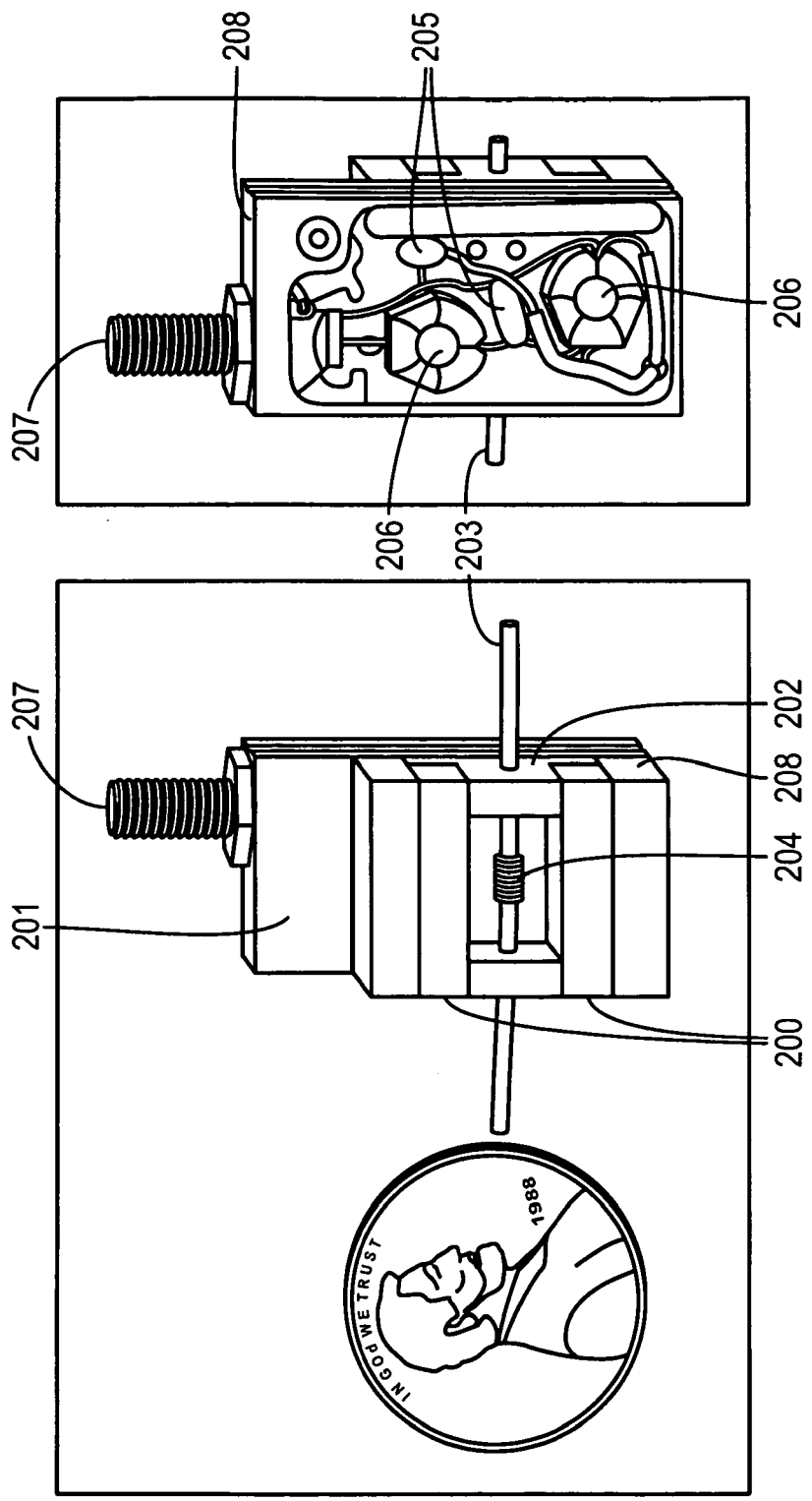
FIG. 2 shows a probehead employing two NdFeB permanent magnets and a ten-turn radiofrequency coil from two sides.
Figure 3:
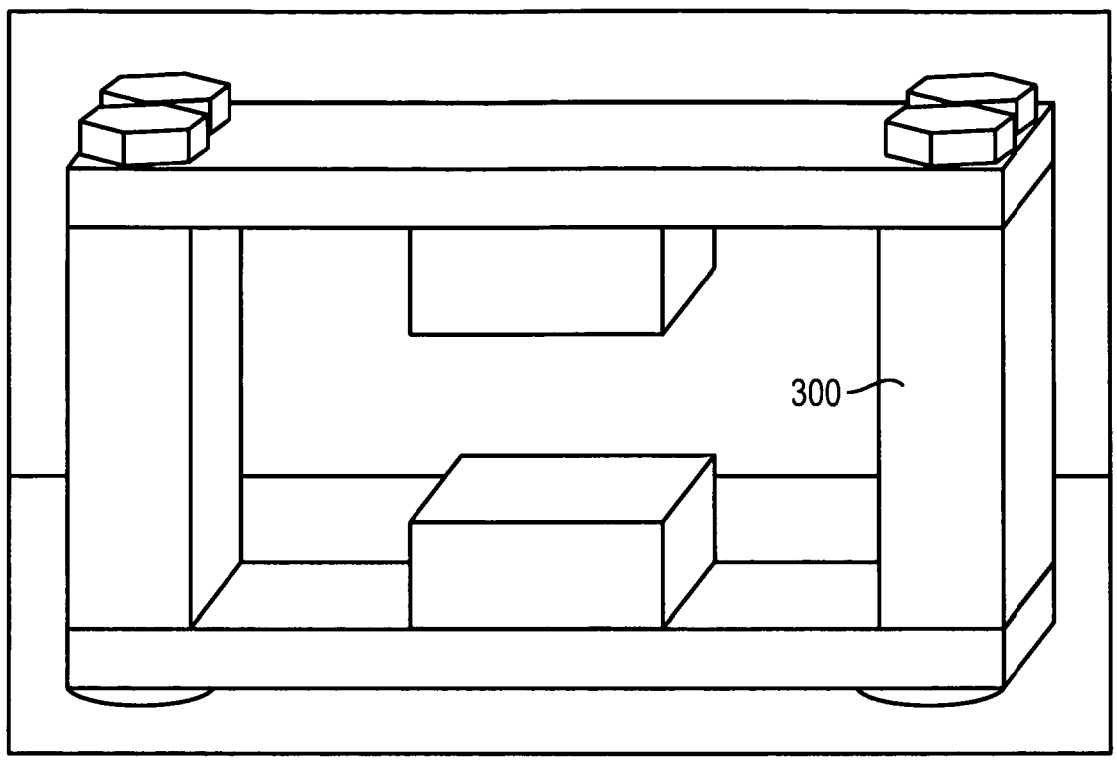
FIG. 3 shows the "T2-yoke" made from a steel yoke and 1"×1"×0.5" NdFeB magnets.
Figure 4:
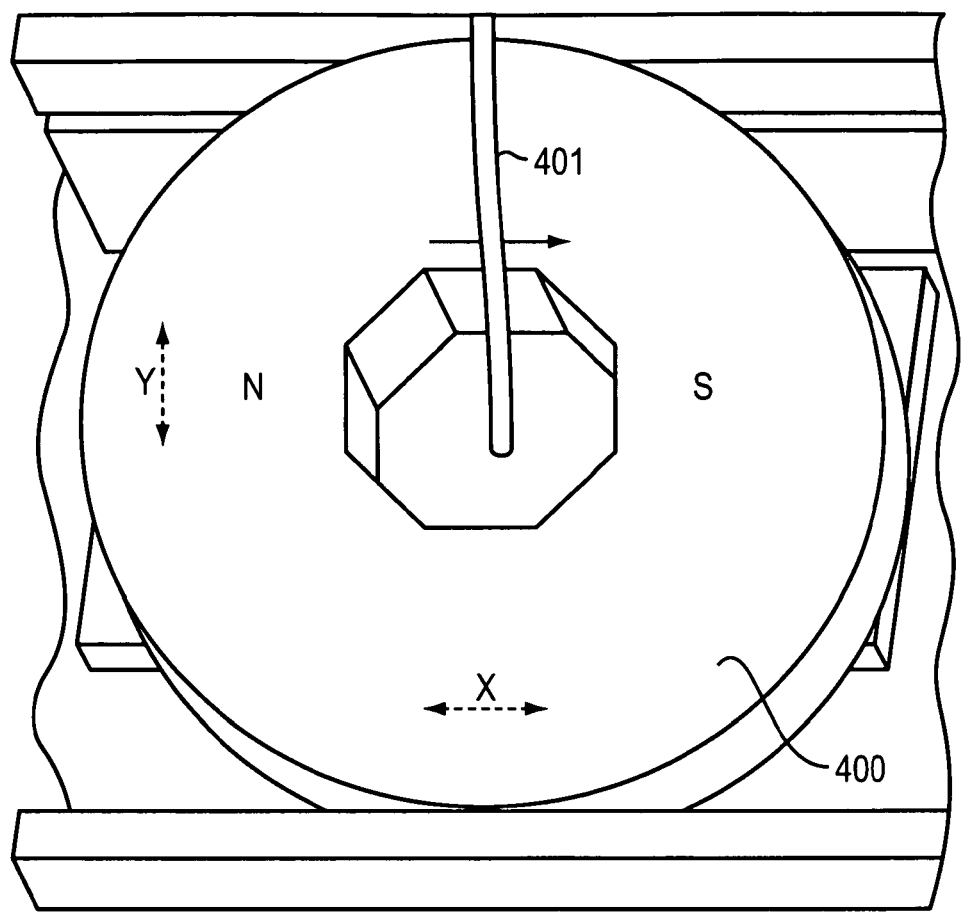
FIG. 4 shows a Halbach magnet positioned on a field mapping apparatus with a gaussmeter probe positioned within the center gap.

For a given magnet configuration, for example, two opposing permanent magnets as presented schematically in FIG. 1 and shown in FIGS. 2 and 3, and a Halbach magnet as shown in FIG. 4, the magnetic field in the x, y, and z directions can be determined using standard methods known in the art, for example, by fixing a gaussmeter probe relative to the magnet and moving the magnet in incremental steps with a three axis stage while recording the field strength as a function of position to obtain a field map.

Given knowledge of the magnetic field, for example, in terms of a calculated or measured magnetic field map and a pulse length of a radiofrequency pulse to be used in relaxation measurements, a radiofrequency coil or radiofrequency coil array can be designed and concurrently a proper position for the same be determined. Pulse length and excitation bandwidth are inversely related. For example, a 2 μs pulse corresponds to a 500 kHz excitation bandwidth (see below for more details). The excitation bandwidth can be used to calculate: 1) for a given sample volume, the necessary magnetic field homogeneity to be able to excite part of or an entire sample volume, and/or 2) for a given magnet or magnet array, the volume that is excitable with a radiofrequency pulse of a given pulse length in the presence of the magnetic field of the given magnet or magnet array.

Typically, a given excitation bandwidth dictates a requisite magnetic field homogeneity. Once a magnet is designed to create limited homogeneity of a volume that is suitable or desirable for a sample (e.g., which may be dictated by fluidics or specimen size of a sample), a coil is designed to excite a complete volume of excitable spins of a sample volume. Thus, according to the present invention, an excitation bandwidth appropriate for a magnet configuration guides the magnet and coil design as well as the probehead configuration design.

A probehead of the present invention includes (a) at least one magnet or magnetic field generator providing a magnetic field; (b) a space capable of accommodating a sample volume having an associated excitable volume; and (c) a radiofrequency coil having an associated detection volume, the radiofrequency coil being adapted and positioned such that its detection volume overlaps at least partly with the excitable volume. The magnetic field provided by the magnet or magnetic field generator is inhomogenous. The space accommodating the sample volume and the radiofrequency coil are adapted and positioned according to a radiofrequency pulse bandwidth optimized for a magnetic field distribution corresponding to the position of the sample volume. The probehead is thus optimized to obtain relaxometry parameters from a sample contained in the detection volume.

An "excitable volume" as used herein is a volume of hydrogen nuclei of water within a sample volume which are transitioned to a higher energy state by a radiofrequency pulse of a given pulse length in the presence of a magnetic field provided by a magnet and/or magnet field generator.

All atomic nuclei with an odd atomic mass or an odd atomic number (like hydrogen nuclei of water for example) possess an intrinsic nuclear magnetic momentum. When such atomic nuclei are placed in a static magnetic field, this momentum can take at least two different orientations. For spin ½ nuclei, such as $^1$H the momentum may take either a parallel or anti-parallel orientation relative to the magnetic field. Considering a population of hydrogen nuclei immersed in the same static magnetic field, the number of nuclei having a parallel orientation is slightly greater than the number of nuclei having an anti parallel orientation (a ratio of 1,000,003: 1,000,000 at fields of 0.5 T and room temperature). This is due the fact that the parallel orientation is only slightly more energetically favorable. Transitions from a parallel state to an anti-parallel state occur when nuclei absorb electromagnetic energy at a given frequency called a resonance frequency, which is dictated by the strength of the magnetic field. Typically, hydrogen nuclei in different locations in a magnetic field experience different magnetic field strengths and therefore have different resonance frequencies required for excitement. Therefore, in prior systems, a range of frequencies were necessary to sufficiently excite a significant portion of hydrogen nuclei in a sample and generate effective relaxation readings. A given pulse length produces a corresponding excitation bandwidth that, at a given magnetic field, excites a volume of hydrogen nuclei with a radiofrequency pulse. The resulting signal after excitation can be detected via typical methods known in the art.

In one embodiment, a RF coil included in a probehead of the present invention is adapted to provide pulse lengths between about 0.4 µs and about 10 µs. Typically, a pulse length of between about 0.5 µs and about 4 µs is used. More typically, a pulse length of between about 1 µs and about 4 µs is used. Even more typically, a pulse length of between about 1 µs and about 3 µs is used.

A "probehead" as used herein is a sensing or probing device of a nuclear magnetic resonance system. A probehead may be implanted, partially or completely, in a mammal's body. Typically, a probehead of the present invention includes (a) at least one magnet and/or magnetic field generator providing a magnetic field, and (b) a radiofrequency coil having an associated detection volume, and the radiofrequency coil being positioned such that its detection volume overlaps at least partly with an excitable volume.

In one embodiment, a probehead comprises a space capable of accommodating a sample volume and/or a port. In certain embodiments, a space capable of accommodating a sample volume and port can be, for example, a radiofrequency coil (as part of a radiofrequency circuit) wound to enclose a sample volume while providing an opening (i.e., space capable of accommodating a sample volume) to allow a sample volume to be placed within the opening. In other embodiments, a space capable of accommodating a sample volume and/or port is distinct from the opening of a radiofrequency coil but adapted to a given radiofrequency coil, for example, formed to enclose part or all of a detection volume of the radiofrequency coil. For example, a glass capillary within a radiofrequency coil.

In some embodiments a radiofrequency coil is wound to enclose a volume of less than about 500 µl. In certain embodiment a radiofrequency coil is wound to enclose a volumes of less than about 100 µl. In still other embodiments a radiofrequency coil is wound to enclose a volume of less than about 10 µl are used. In still further embodiment a radiofrequency coil is wound to enclose a volume of less than about 5 µl. In particular embodiments a radiofrequency coil is wound to enclose a volume of less than about 1.6 µl. In still further particular embodiments a radiofrequency coil is wound to enclose a volume of less than about 0.4 µl.

Also, for implantable probeheads, typically, material used to form a sample volume, and, in particular, any material that may be in contact with a biological sample or tissue is typically biocompatible, that is constructed of materials that allow for proper function of both the device and a host animal's biological functions and/or coated with a physiologically acceptable coating as known in the art to render the implantable bioinert, biomimetic, or bioactive, as desired.

Suitable materials include titanium, inert silicone elastomers, ceramics, glass, polymeric materials, poly-β-hydroxybutyrate (PHB) and the like. One or more sample volumes and corresponding ports can be fabricated using methods known in the art. Suitable methods include form or injection molding methods, and microfabrication methods for sample containers smaller than a few millimeter, for example, two-photon three-dimensional lithography. A probehead may contain a "housing" that encloses the components of the probehead such as, for example, a radiofrequency coil and magnet. In certain embodiments at least one component of a probehead (e.g., a magnet, a magnetic field generator, a radiofrequency coil) is attached to the housing.

A "port" as used herein, refers in the simplest case to an opening as provided above, but can also be a structure or device that is adapted to selectively allow analytes or reagents to enter and/or exit the sample volume.

In certain embodiments, a probehead includes one or more separate sample volumes. In some embodiments a probehead includes between about 1 and about 100 sample volumes. In some embodiments a probehead includes between about 1 and about 10 sample volumes. In some embodiments a probehead includes two sample volumes. In certain embodiments a probehead includes one sample volume.

A probehead containing more than one sample volume may comprise a radiofrequency coil with an associated detection volume encompassing at least part of each sample volume. Alternatively, a probehead may have more than one radiofrequency coil and/or radiofrequency circuit, one for each sample volume or a subgroup of the sample volumes. In certain embodiments, a probehead comprises at least two radiofrequency coils. Also, a probehead of the systems of the present invention can include a magnet or magnetic, field generator as discussed above.

For probeheads that include a plurality of separate sample volumes but only one radiofrequency coil that is employed to probe the plurality of sample volumes simulatenously, multiplexing methods may be used to distinguish the magnetic resonance signal or information from the separate sample chambers. For example, one multiplexing method that may be used is based on extracting decay constant values, for example, values of spin-spin relaxation constant $T_2$ from multi-exponential relaxation curves (see T. J. Lowery et al., Anal. Chem. (2008), 80, 1118-1123.). Relaxation data obtained using a probehead of the present invention may be fit to a decaying exponential curve defined by the following equation:

$$f(t) = \sum_{i=1}^{n} A_i \exp(-t/T(i))$$

where f(t) is the signal intensity as a function of time, t, $A_i$ is the amplitude coefficient for the ith component, and $(T)_i$ the decay constant (such as $T_2$) for the ith component. For relaxation phenomenon discussed here the detected signal is the sum of a discrete number of components (i=1, 2, 3, 4 ... n). Such functions are called mono-, bi-, tri-, tetra- or multi-exponential, respectively. Due to the widespread need for analyzing multi-exponential processes in science and engineering, there are several established mathematical methods for rapidly obtaining estimates of $A_i$ and $(T)_i$ for each coefficient (Istratov, A. A. & Vyvenko, O. F. 1999. Exponential analysis in physical phenomena. *Rev. Sci. Inst.* 70 (2): 1233-1257).

A "magnet" as used herein can be any material or combination of materials that provides a magnetic field in at least some volume around the material. Typically, the magnet is a permanent magnet. Suitable, materials include but are not limited to NdFeB, FeCo, and the like. Magnets can be configured to form new magnets, that is, magnet arrays, for example, a permanent magnet with a c-shaped yoke, a Halbach magnet (cylinder and other configurations), u-magnet, torroidal magnet and the like.

The magnets, magnet configurations and magnetic field generators of the present systems can be weak and/or provide magnetic fields that are inhomogeneous. Typically, maximum magnetic field strength values provided by the magnets and/or magnet configurations of the present invention are between about 0.2 Tesla and about 2 Tesla. More typically, they are between about 0.3 and about 1.5 Tesla. Even more typically, they are between about 0.4 and about 1.1 Tesla. Even more typically, they are between about 0.2 and about 1.1 Tesla. Even more typically, they are between about 0.2 and about 0.8 Tesla. Most typically, they are between about 0.45 and 0.85 Tesla. In some embodiments the magnetic field strength is less than about 2 Tesla. In certain embodiments the magnetic field strength is less than about 1.1 Tesla. In certain embodiments the magnetic field strength is less than about 0.8 Tesla.

The term "inhomogeneous" refers to magnetic fields that are lower in uniformity than those required for spectroscopy. Homogeneity is dependent on the space in which the measurement is defined. For the instant applications, homogeneities of the magnetic fields can range between about 10000 ppm and about 10 ppm. in some embodiments homogeneities can range between about 50 ppm and 5000 ppm. In particular embodiments homogeneities can range between about 100 ppm and about 1000 ppm.

Also, typically, magnetic fields employed in the present systems are effectively static, that is, they do not change substantially over time. Changes in magnetic field such as due to temperature fluctuations are considered to be not substantial.

Small probeheads of the present invention can be used for, but are not limited to in-vivo magnetic resonance measurements. Small probeheads for complete implantation within a mammal's body, preferably have small magnets to lessen the invasiveness of the implantation. Typically, magnets for implantation are smaller than about 2 inches in any dimension. More typically, magnets for implantation are smaller than about 1 inch in any dimension. Most typically, magnets for implantation are smaller than about 0.5 inches in any dimension.

The probeheads of the present invention can also be used in-vitro, for example, as part of small and/or portable magnetic resonance systems. Typically, magnets in probeheads for these systems are smaller than about 2 inches in any dimension. More typically, they are smaller than about 1 inch in any dimension. Most typically, they are smaller than about 0.5 inches in any dimension. Each dimension may be independently determined.

A "magnetic field generator" as used herein, is a device that provides a magnetic field in at least some volume around the device. Typically, a magnetic field generator requires a power supply and provides the targeted magnetic field only when powered. Examples of magnetic field generators include but are not limited electromagnets with and without a metal pole (see Cardot et al Sensors and Actuators 1994).

Probeheads using magnetic field generators can be implanted in a mammal's body. However, because magnetic field generators tend to be larger than magnets, and they are more complex, for example, require a power supply, more typically, probeheads using magnetic field generators are used for disposition outside a mammal's body.

The magnet(s) and magnetic field generator(s) in the present systems are selected and positioned to provide a magnetic field of sufficient strength in the sample volume to allow measuring magnetic resonance signals. The magnetic field strength of a given magnet or magnetic field generator in a given volume, for example, a sample volume can be calculated and/or approximated using methods known in the art. Typically, the magnetic field strength depends on the nature of the magnet or magnetic field generator and the position of the magnet or magnetic field generator relative to the sample volume. Also, magnetic field strength of a given magnet or magnetic field generator in a sample volume can be measured using methods and devices known in the art, for example, gaussmeters, teslameters, hall effect probes, and the like. Typically, magnetic field strengths within a sample volume of between about 0.2 and about 2 Tesla are sufficient to allow measuring magnetic resonance signals. More typically, magnetic field strengths within the sample volume of between about 0.2 and about 1 Tesla are sufficient to allow measuring magnetic resonance signals. Even more typically, magnetic field strengths within the sample volume of between about 0.2 and about 0.8 Tesla are sufficient to allow measuring magnetic resonance signals. Most typically, magnetic field strengths within the sample volume of between about 0.3 and about 0.65 Tesla are sufficient to allow measuring magnetic resonance signals.

The magnets and magnetic field generators suitable for the probeheads of the present invention are not limited to any particular size. However, in particular, for implantable and handheld probeheads small magnets are desired. Typically, each of the at least one magnet or magnetic field generator of the probeheads of the present invention is in any dimension less than about one two inches. More typically, each of the at least one magnet or magnetic field generator is in any dimension less than about 1 inch. Most typically, each of the at least one magnet or magnetic field generator is in any dimension less than about 0.5 inch.

Probeheads of the present invention may be used to sense/measure magnetic resonance signals as part of a magnetic resonance system with sensing reagents enclosed within the probehead, and, in particular, within one or more sample volume.

A "sensing agent" as used herein is an agent that senses, responds to or is influenced by a sample characteristic to correlate the presence and/or extent of the sample characteristic with the presence, change or magnitude of the magnetic resonance signals associated with the sample. The term "sample characteristic" as used herein refers to any chemical and/or physical property of a given sample. Suitable sample characteristics can be, but are not limited to concentration of an analyte (that is, a molecule, ion, or radical of interest in the sample), pH-value, ionic strength, hydration state (e.g., of tissue or biofluids, that is, concentration of water in tissue or biofluids), temperature, and the like.

Suitable sensing agents can be, but are not limited to dry reagent compositions, magnetic particles, responsive polymers, magnetic resonance contrast agents, and the like.

Dried reagent compositions that are suitable include, for example, dried biotinylated coated nanoparticles (see T. J. Lowery et al., Anal. Chem. (2008), 80, 1118-1123), for example, based on the following formulation (216 μL, 0.083 mM Fe, 10 mM PBS, 20 mg/ml dextran, pH 7.4). Dried reagent compositions can be prepared by placing a magnetic particle solution, for example, biotinylated coated nanoparticle solution into a container, for example, a container such as a glass tube, and freezing the container in a freeze dryer (e.g., VirTis freeze dryer (Gardiner, N.Y.)), for example, at −80° C. for 24 h. Each of the one or more separate volumes of the sample containers may be filled by transfer of the dried reagent composition from the container that was used during freeze drying.

"Magnetic particles" as used herein, are particles that respond to or are influenced by a sample characteristic to correlate the presence and/or extent of the sample characteristic with the presence, change or magnitude of the magnetic resonance signals associated with the sample. Typically, the magnetic particles respond by aggregating. Also, typically, magnetic particles have an average particle size of between about 1 nm and 5 µm. Magnetic particles may be paramagnetic or superparamagnetic. They can have binding moieties on their surface. The binding moieties are preferably operative to alter the aggregation of the magnetic particles as a function of the presence or concentration of the analyte. The magnetic particles may include an oxide and/or a hydroxide of Fe, Si, Sn, An, Ti, Bi, Zr, and/or Zn. The magnetic particles are preferably superparamagnetic and have crystallite size from about 1 nm to about 100 nm. The magnetic nanoparticles preferably have a metal oxide core of about 1 to about 25 nm, from about 3 to about 10 nm, or about 5 nm in diameter. The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria. For example, in one embodiment, the binding moieties may include one, two, or more types of oligonucleotides and/or one, two, or more types of proteins. The binding moieties may be a polymer, or may be part of a polymer that is linked to, or otherwise associated with one or more of the magnetic particles. The binding moieties preferably include functional groups, for example, the binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group.

The analyte may include one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include, for example, a lipid, a gas (e.g., oxygen, carbon dioxide), an electrolyte (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, and/or a lipopolysaccharide.

For example, magnetic particles can be adapted to respond to glycated hemoglobin. For example, amino-CLIO nanoparticles, that is, iron oxide nanoparticles coated with amino-functionalized cross-linked dextran, may be decorated with boronate compounds by standard solution-phase chemistries. The boronate compounds such as boronic acid, phenylboronic, boric acid and boronate, etc. have an affinity for HbA1c, a specific type glycated hemoglobin designated based on its separation from other species of glycated hemoglobin. Hemoglobin is composed of four subunits, two α chains and two β chains therefore HbA1c is divalent. The divalency allows HbA1c to facilitate the boronic acid functionalized superparamagnetic iron oxide particle agglomeration. Boronate reacts with HbA1c in a sample through the cis-diol moiety of glucose bound to hemoglobin, forming a five-membered ring structure. A boronate group can be attached to a solid phase covalently or electrostactically by a variety of chemistries. Solid phases such as amino-CLIO nanoparticles can be decorated with boronate compounds by standard solution-phase chemistries. Amino-CLIO are iron oxide nanoparticles coated with amino-functionalized cross-linked dextran. The dextran polymer coating endows these nanoparticles with solubility and enabled solution-phase chemistries. Suitable boronate compounds include but are not limited to 4-carboxyphenylboronic acid, 3-nitro-5-carboxyphenylboronic acid, and m-aminophenylboronic acid (APBA).

"Nanosensors" are paramagnetic or superparamagnetic magnetic particles, typically of nanometer scale, that comprise a polymer matrix layer about a magnetic core and/or are derivatized/functionalized with binding moieties or affinity groups for a target compound or analyte. Suitable nanosensors include responsive polymer-coated magnetic nanoparticles. These nanosensors can exploit the ability of magnetic nanoparticles to dephase nuclear spins detectable by nuclear magnetic resonance (NMR), hereinafter generally exemplified as the protons of water molecules, for detection without aggregation of nanoparticles. Each nanoparticle has a polymer matrix layer which expands or contracts when exposed to an analyte and/or condition to be detected. The resulting change in nanoparticle size affects the dephasing of freely-diffusing water molecules in the vicinity of the nanoparticles, which affects one or more NMR-detectable properties. By calibrating the NMR-detected properties with known reference samples, the existence of the condition and/or analyte of interest may be detected in test samples via NMR techniques using the probeheads of the present invention.

In the case where the detected nuclei are water protons, the polymer matrix preferably takes the form of a stimuli or molecule sensitive hydrogel comprising a polymer "mesh" that is cross-linked by binding moieties that affects the volume, permeability and the proton content of the matrix as a function of a physical or chemical stimulus or a physical parameter of the analyte under study. This is accomplished by design of the matrix as a hydrophilic polymer network comprising (as pendent groups or as part of the polymer backbone) binding moieties that influence water permeability (and/or permeability of other molecules in the environment) through formation of one or more covalent or hydrogen bonds, van der Waals interactions, or physical entanglement with a component of the analyte. The presence of analyte induces a change in the crosslink density of the polymer, which leads to a change in the volume fraction of the solution occupied by the polymer. The change in cross link density also leads to a change in the diameter of the nanoparticles, which leads to a change in their diffusion time. Both diffusion time and specific volume are proportional to the $T_2$ relaxivity observed for a solution, as shown in the proportionality:

$$1/T_2 \alpha (V_p)(R^2/D)$$

where $V_p$ is the specific volume fraction of the particles in solution, R the radius of the particles, and D the diffusion constant of water. The term $R^2/D$ is equal to the diffusion time, $\tau_d$. This is the time necessary for a water molecule to diffuse past a particle, and is proportional to the extent of $T_2$ relaxation that occurs.

The binding moiety may be a chemical binder, an electroactive mediator, an electron-pair donor, and/or an electron-pair acceptor. It may contain an amino, carboxyl, sulfhydryl, amine, imine, epoxy, hydroxyl, thiol, acrylate, or isocyano group, or a mixture thereof. For example, the binding moiety may be an acetic acid moiety such as in poly(acrylic acid) for sensing pH, or phenylboronic acid for sensing the presence of diols, such as glucose Alternatively, the binding moieties are binding pairs, or binding pendants, such as antibodies that serve as cross-linkers in the presence of their cognate antigen, or antigens that serve as cross-linkers in the presence of their cognate antibodies, and which mediate the water proton flux in and out of the matrix and change in specific volume by competitive affinity reactions. This typically is accomplished as the extent of cross-linking of matrix polymer is mediated as a function of the physical parameter under study so as to control the permeability of water, including its amount and rate of translational diffusion in an out of the matrix and within the matrix volume in proximity to the magnetic particle(s). For example, the binding pairs may be a ligand binding protein such as concanavalin A bound to a low-affinity ligand such as a carbohydrate. Addition of glucose to this system would displace the low affinity ligand and change the crosslinking of the matrix. Another example is a matrix-immobilized antibody, antibody fragment, or peptide that crosslinks the matrix by binding to its matrix-immobilized antigen or target. The presence of a higher affinity analyte would lead to disruption of the cross-linked matrix and a swelling of the matrix.

The responsive matrix may comprise a matrix of material which includes one or more monomers and/or polymers. The one or more monomers and/or polymers contains functional groups that enable the binding moiety to be attached to or otherwise in stable association with the nanoparticle to form the conjugate. The polymer can be a natural polymer, a synthetic polymer, a combination of natural and synthetic polymers, shape memory polymers, block co-polymers (PEO, PPO), or derivatives of each type. For example, the matrix polymer may be poly (N-isopropylacrylamide). The matrix polymer may also be (or include), for example, Poly(N-isopropylacrylamide) (PNIAAm), Poly(N,N-diethyacrylamide) (PDEAAm), P(NIAAm-co-BMA), PEO-PPO-PEO (e.g., Pluronic®), N,N-diethylaminoethyl methacrylate (DEA), 2-hydroxypropyl methacrylate (HPMA), Poly-(methacrylic acid-g-ethylen glycol), Poly(2-glucosyloxyethyl methacrylate), Poly(N-vinyl-2pyrrolidone-co-3-(acrylamido)phenylboronic acid), and/or N-(S)-sec-butylacrylamide. The functional groups can be any appropriate chemical functional group, e.g. carboxy, amino, or sulfhydryl groups. A specific moiety or moieties may be attached to the nanoparticle via conjugation to these groups, or by physical adsorption and/or through hydrogen bonds or van der Waals interactions. The responsive polymer matrix, through physical and/or chemical stimuli, mediates the specific volume of the polymer layer, leading to a detectable change in NMR-measurable properties such as $T_2$ relaxivity.

"Responsive polymers" (also referred to herein as "smart polymers") are polymers that are, for example, sensitive to pH, ionic strength, and specific molecular and biomolelar analytes. In these cases the hydration level, cross-link density, or other characteristic of the polymer changes in response to a changes in the sample, for example, biofluid. This change in polymer state leads to changes in the magnetic resonance signals that can be detected by an implanted radiofrequency coil. Suitable smart polymers are known in the art, and described, for example, in Gemeinhart, R A, Chen, J, Park, H, Park, K. 2000. pH-sensitivity of fast responsive superporous hydrogels. J. Biomater. Sci. Polym. Ed. 11: 1371-1380; Murakami, Y, Maeda, M. 2005. DNA-responsive hydrogels that can shrink or swell. Biomacromolecules, 6: 2927-2929; Miyata, T, Uragami, T, Nakamae, K. 2002. Biomolecule-sensitive hydrogels. Adv Drug Deliv Rev, 54: 79-98; and Zhang, R, Bowyer, A, Eisenthal, R, Hubble, J. 2006. A smart membrane based on an antigen-responsive hydrogel. Biotechnol Bioeng.

Probeheads of the present invention include a radiofrequency coil.

A "radiofrequency coil" as used herein is a is a coil that is suited to sense and/or detect magnetic resonance signals in an associated detection volume, and, optionally, also allows to apply/emit radiofrequency pulses with associated pulse length(s) to a sample under investigation with the probehead as part of a magnetic resonance system. Suitable radiofrequency coil types include planar coils and "whole volume" coils such as might be constructed of opposed saddle coils, solenoids, Helmholtz coils and the like. Typically, the probeheads employed in the systems of the present invention include solenoids.

"Detection volume" as used herein refers to a volume associated with a given radiofrequency coil from which magnetic resonance signals, in principle, are detectable with the given radiofrequency coil as part of a given magnetic resonance system. "Detectable" as used herein refers to distinguishable from the background noise level, that is, a magnetic resonance signal is detectable if a signal can be distinguished from background noise level with a given radiofrequency coil as part of a given magnetic resonance system. The detection volume for a given radiofrequency coil-magnetic resonance system combination can be calculated, approximated and/or measured using methods known in the art. Typically, however, it is sufficient to approximate the detection volume. For example, for a solenoid coil, typically, the detection volume is effectively, the volume enclosed within the coil, which, typically, is of about cylindrical shape. In certain embodiments a radiofrequency coil is a cylinder shape. Thus, for a solenoid a good approximation of the detection volume is the volume of the enclosed cylinder, which can be calculated very easily. Similar approximations are known in the art for other types of radiofrequency coils (see, e.g., Mispelter, J., Lupu, M., Briquet, A. "NMR Probeheads for biophysical and biomedical experiments" 2006 Imperial College Press, London.). In certain embodiments a radiofrequency coil is wound to enclose a coil volume having a shape of about cylindrical shape and the associated detection volume is effectively the volume of the cylindrical shape. In some embodiments a radiofrequency coil is positioned to have the coil volume include between about 80 percent and about 100% of the excitable volume. In still other embodiments a radiofrequency coil is positioned to have the coil volume include effectively all of the excitable volume.

"Sensitive volume" as used herein refers to the overlap volume between the excitable volume and the detection volume, and is the volume from which magnetic resonance signals can be detected with the radiofrequency coil. A sensitive volume is determined by a fill factor (i.e., a fraction of the detection volume of an RF coil which is filled with a sample volume).

In some embodiments, a fill factor is between about 10 percent and about 100 percent. In certain embodiments a fill factor is between about 50 percent and about 100 percent. In some embodiments the fill factor is about 80 percent. In certain embodiments the fill factor is effectively 100 percent. In some embodiments a fill factor is at least about 0.1, at least about 0.5, at least about 0.75, at least about 0.9, and or about 1.

Typically, a detection volume includes between about 10 percent and about 100 percent of the excitable volume. More typically, a detection volume of a given radiofrequency coil within the probehead includes between about 50 percent and about 100 percent of the excitable volume. Even more typically, a detection volume includes about 80 percent of the excitable volume. Most typically, a detection volume includes effectively all of the excitable volume.

Also, typically, an excitable volume includes between about 10 percent and about 100 percent of the detection volume. More typically, the excitable volume includes between about 50 percent and about 100 percent of the detection volume. Even more typically, the excitable volume includes between about 80 percent and about 100 percent of the detection volume. Most typically, the excitable volume includes effectively all of the detection volume.

Further, for a given sample volume within the probehead, typically, the sample volume includes between about 10 percent and about 100 percent of the excitable volume. More typically, the sample volume includes between about 50 percent and about 100 percent of the excitable volume. Even more typically, the sample volume includes between about 80 percent and about 100 percent of the excitable volume. Even more typically, the sample volume includes effectively all of the excitable volume. Most typically, the sample volume includes effectively all of the excitable volume and the detection volume includes effectively all of the sample volume.

In some embodiments a sample volume includes effectively all of the excitable volume and a detection volume includes effectively all of the sample volume. In still further embodiments a sample volume includes between about 10 and about 100 percent of the sensitive volume.

Typically, for a magnetic field of between about 0.2 Tesla and 1.1 Tesla, radiofrequency coils with associated detection volumes of less than about 500 µl are used. More typically, radiofrequency coils with associated detection volumes of less than about 100 µl are used. Even more typically, radiofrequency coils with associated detection volumes of less than about 10 µl are used. Even more typically, radiofrequency coils with associated detection volumes of less than about 5 µl are used. Most typically, radiofrequency coils with associated detection volumes of less than about 1.6 µl are used. In some embodiments a radiofrequency coil with associated detection volume of about 1.6 µl is used, and a sample volume of about 0.4 µl is used.

A radiofrequency coil of a given probehead of the present invention senses and/or detects magnetic resonance signals of a sample in the presence of a magnetic field and provides the sensed signals to a processing unit. The processing unit can be included within a probehead, but does not have to be included in a probehead. In any case, a probehead contains any parts, for example, circuitry, logic circuitry, power sources and other parts such as capacitors and the like, as known in the art, to allow the sensed signals to be provided to the processing unit. For example, a probehead of the present invention that is to be used in a magnetic resonance system with a radiofrequency coil of the probehead being inductively coupled to the processing unit via an external pickup coil, typically, includes the radiofrequency coil as part of a radiofrequency circuit with one or more tuning capacitors included in the circuit. In one embodiment a probehead further comprises at least one capacitor, wherein a radiofrequency coil and at least one capacitor are part of a radiofrequency circuit.

One embodiment of the present invention is a probehead for magnetic resonance relaxometry that includes (a) at least one magnet providing a magnetic field, and (b) a radiofrequency coil having an associated detection volume, the radiofrequency coil being adapted and positioned such that its detection volume includes between about 80 percent and about 100 percent of an excitable volume, wherein the magnetic field has a magnetic field strengths of less than about 1.1 Tesla.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume includes between about 80 percent and about 100 percent of an excitable volume, wherein the magnetic field has a magnetic field strengths of less than about 1.1 Tesla.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume includes effectively all of an excitable volume, wherein the magnetic field has magnetic field strengths of less than about 1.1 Tesla.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume includes effectively all of an excitable volume, wherein the magnetic field having magnetic field strengths of less than about 1.1 Tesla, the probehead further comprising a sample volume and the sample volume including between about 10 and about 100 percent of the excitable volume.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume includes effectively all of an excitable volume, wherein the magnetic field having magnetic field strengths of less than about 1.1 Tesla, the probehead further comprising a sample volume, and the sample volume including between about 50 and about 100 percent of the excitable volume.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume overlaps at least partly with an excitable volume, wherein the magnetic field having magnetic field strengths of less than about 1.1 Tesla, the probehead further comprising a sample volume, the sample volume including effectively all of the excitable volume and the detection volume including effectively all of the sample volume.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume overlaps at least partly with an excitable volume, wherein the magnetic field has a magnetic field strengths of less than about 1.1 Tesla, and wherein the probehead further comprises a sample volume, the excitable volume and the detection volume overlapping in a sensitive volume, and wherein the sample volume includes between about 10 and 100 percent of the sensitive volume.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume overlaps at least partly with an excitable volume, wherein the magnetic field having magnetic field strengths of less than about 1.1 Tesla, wherein the probehead further comprises a structure defining a sample volume, the excitable volume and the detection volume overlapping in a sensitive volume, and wherein the sample volume includes between about 50 and 100 percent of the sensitive volume.

Another embodiment of the present invention is a probehead for magnetic resonance relaxometry that includes (a) at least one permanent magnet providing a magnetic field, and (b) a radiofrequency coil having an associated detection volume, the radiofrequency coil being adapted and positioned such that its detection volume overlaps at least partly with an excitable volume, wherein the magnetic field has a magnetic field strengths of less than about 1.1 Tesla, the probehead further comprising a sample volume, the excitable volume and the detection volume overlapping in a sensitive volume, and wherein the sample volume includes effectively all of the sensitive volume.

Another embodiment of the present invention is a probehead for magnetic resonance relaxometry that includes (a) two permanent magnet providing a magnetic field, and (b) a radiofrequency coil having an associated detection volume, the radiofrequency coil being adapted and positioned such that its detection volume overlaps at least partly with an excitable volume, wherein the magnetic field has magnetic field strengths of less than about 1.1 Tesla, wherein the radiofrequency coil is wound around a sample tube or capillary to enclose, the radiofrequency coil and the sample tube or capillary enclosing a sample volume within the sample tube or capillary. In certain embodiments, the excitable volume and the detection volume are overlapping in a sensitive volume, and the sample volume includes between about 50 and about 100 percent of the sensitive volume.

Another embodiment of the present invention is a probehead for magnetic resonance relaxometry that includes (a) two permanent magnet providing a magnetic field, and (b) a radiofrequency circuit comprising (1) a radiofrequency coil and (2) a capacitor, the radiofrequency coil having an associated detection volume and the radiofrequency coil being adapted and positioned such that its detection volume overlaps at least partly with an excitable volume, wherein the magnetic field has magnetic field strengths of less than about 1.1 Tesla, the radiofrequency coil being wound around a sample tube or capillary to enclose, the radiofrequency coil and the sample tube or capillary enclosing a sample volume within the sample tube or capillary, the excitable volume and the detection volume overlapping in a sensitive volume, and the sample volume includes between about 50 and about 100 percent of the sensitive volume.

Another embodiment of the present invention is a probehead for magnetic resonance relaxometry that includes (a) two permanent magnet attached to a yoke providing a magnetic field, and (b) a radiofrequency circuit comprising (1) a radiofrequency coil and (2) a capacitor, the radiofrequency coil having an associated detection volume and the radiofrequency coil being adapted and positioned such that its detection volume overlaps at least partly with an excitable volume, wherein the magnetic field has magnetic field strengths of less than about 1.1 Tesla, the radiofrequency coil being wound around a sample tube or capillary to enclose, the radiofrequency coil and the sample tube or capillary enclosing a sample volume within the sample tube or capillary, the excitable volume and the detection volume overlapping in a sensitive volume, and the sample volume including between about 50 and about 100 percent of the sensitive volume. Other specific embodiments of the present invention are the probeheads as described in the preceding paragraphs, wherein a probehead is adapted for a pulse length of between about 0.4 microseconds and about 10 microseconds, between about 1 microsecond and about 4 microseconds, or between about 1.5 microseconds and 2.5 microseconds, and, independently, each magnet is independently in any dimension less than about two inches, less than about 1 inch, or less than about 0.5 inch. Other embodiments of the present invention include methods of preparing probeheads provided and described in the preceding paragraphs, and the examples which follow. In one embodiment is a method for preparing a probehead for use in a magnetic resonance relaxometer. The method comprises the steps of (a) providing at least one magnet or magnetic field generator providing a magnetic field, (b) providing a radiofrequency coil, (c) positioning the radiofrequency coil to have its associated detection volume overlap at least partly with an excitable volume, (d) positioning a space capable of accommodating a sample volume having an associated excitable volume; and (e) adapting the space for the sample volume and the radiofrequency coil according to a radiofrequency pulse optimized for the magnetic field distribution corresponding to the position of the detection volume. The probehead is thus optimized to obtain relaxometry parameters from a sample contained in the sample volume.

Another embodiment is a method of preparing a small probehead for use in portable magnetic resonance relaxometry. The method comprises the steps of (a) attaching two magnets or two magnetic field generators to a yoke such that the south pole surface of one of the magnets or magnetic field generators opposes the north pole surface of the other magnet or magnetic field generator to form a gap between the magnets or magnetic field generators and to provide a magnetic field in the gap, (b) positioning a space capable of accommodating a sample volume having an associated excitable volume, and (c) positioning a radiofrequency coil within the gap, the radiofrequency coil having an associated detection volume and being adapted to emit a radiofrequency pulse with a pulse length, the radiofrequency coil being positioned and designed to have the detection volume at least partly overlap with an excitable volume within the gap. The probehead is thus optimized to obtain relaxometry parameters from a sample contained in the sample volume.

In a further embodiment a method of preparing a small probehead for use in a portable magnetic resonance relaxometer further comprises the step of providing, calculating, and/or measuring a magnetic field map of the at least one magnet or magnetic field generator, and further wherein the step of providing the radiofrequency coil comprises selecting or manufacturing a radiofrequency coil dimensioned based on the magnetic field map to optimize its associated detection volume be at least as large as the excitable volume.

In another further embodiment a method of preparing a small probehead for use in a portable magnetic resonance relaxometer further comprises the step of providing, calculating or measuring a magnetic field map of the at least one magnet or magnetic field generator, and further wherein the step of positioning the radiofrequency coil is based on the magnetic field map to optimize its associated detection volume overlap at least partly with the excitable volume.

In yet another further embodiment a method of preparing a small probehead for use in a portable magnetic resonance relaxometer further comprises the step of providing, calculating or measuring a magnetic field map of the at least one magnet or magnetic field generator, and further wherein providing the radiofrequency coil comprises selecting or manufacturing a radiofrequency coil dimensioned based on the magnetic field map to have its associated detection volume be at least as large as the excitable volume, and positioning the radiofrequency coil is based on the magnetic field map to have the associated detection volume overlap at least partly with the excitable volume.

EXEMPLIFICATION

Example 1

The probehead of FIG. 2 (also referred herein as "Abe" probehead) was fabricated from a custom machined c-shaped yoke 208 (0.688"×0.5"×0.438", steel), custom machined electronics enclosure 201 (1"×0.5"×0.5", aluminum), coil holders 202 (0.19"×0.19", teflon), magnet positioner (0.438"×0.5"×0.063", Teflon), sample tube 203 (1 mm O.D., 0.5 mm I.D., 0.6" long, Teflon), and ten-turn RF coil 204 (32 gage enamel coated copper wire, hand-wound, fastened to the sample tube by lock-tite instant adhesive). The resonant circuit was constructed by a 10-120 pF variable matching capacitor 206, and a combination of a 10-120 pF variable capacitor 206 and two fixed capacitors 205, and a bulkhead SMA connector 207.

Figure 5:
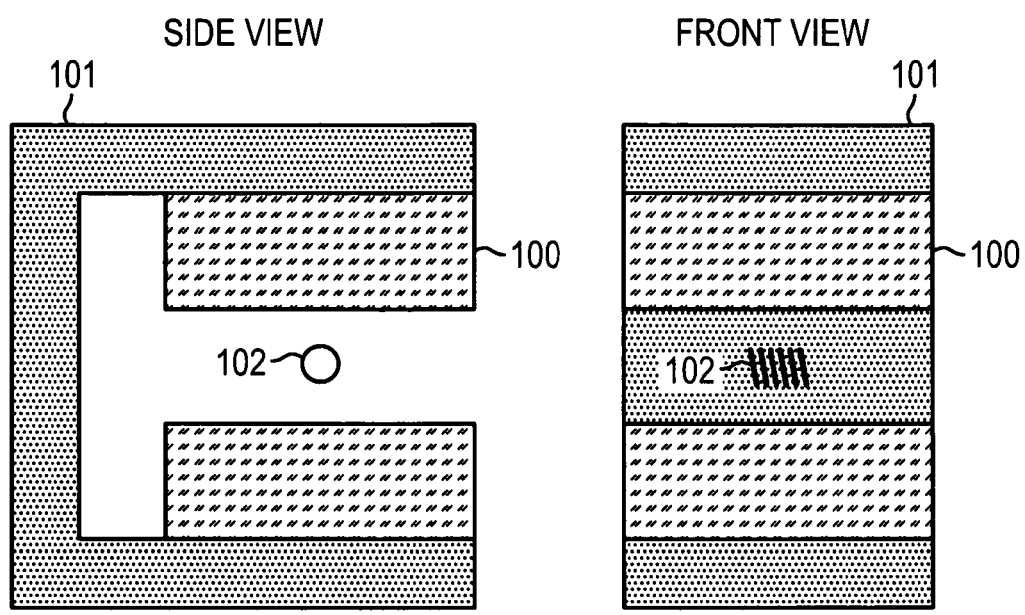
FIG. 5 provides a schematic representation (side view and front view) of a probehead including a c-shaped yoke with magnets attached thereto and a radiofrequency coil placed between the magnets.

Two inexpensive, off-the-shelf permanent magnets made of NdFeB 200 were attached to the steel yoke 208 as shown schematically in FIGS. 1 and 5. (FIGS. 1 and 5 show two magnets 100 attached to a c-shaped yoke 101 and a radiofrequency coil 102 positioned between the magnets). The size of the magnets was ¼"×⅛"×½", magnetized along the ⅛" axis. The largest dimension of the array, including the supporting yoke was ½". It is believed that the steel yoke helps driving the magnetic flux between the magnet blocks, following the path of high magnetic permeance.

Figure 6:
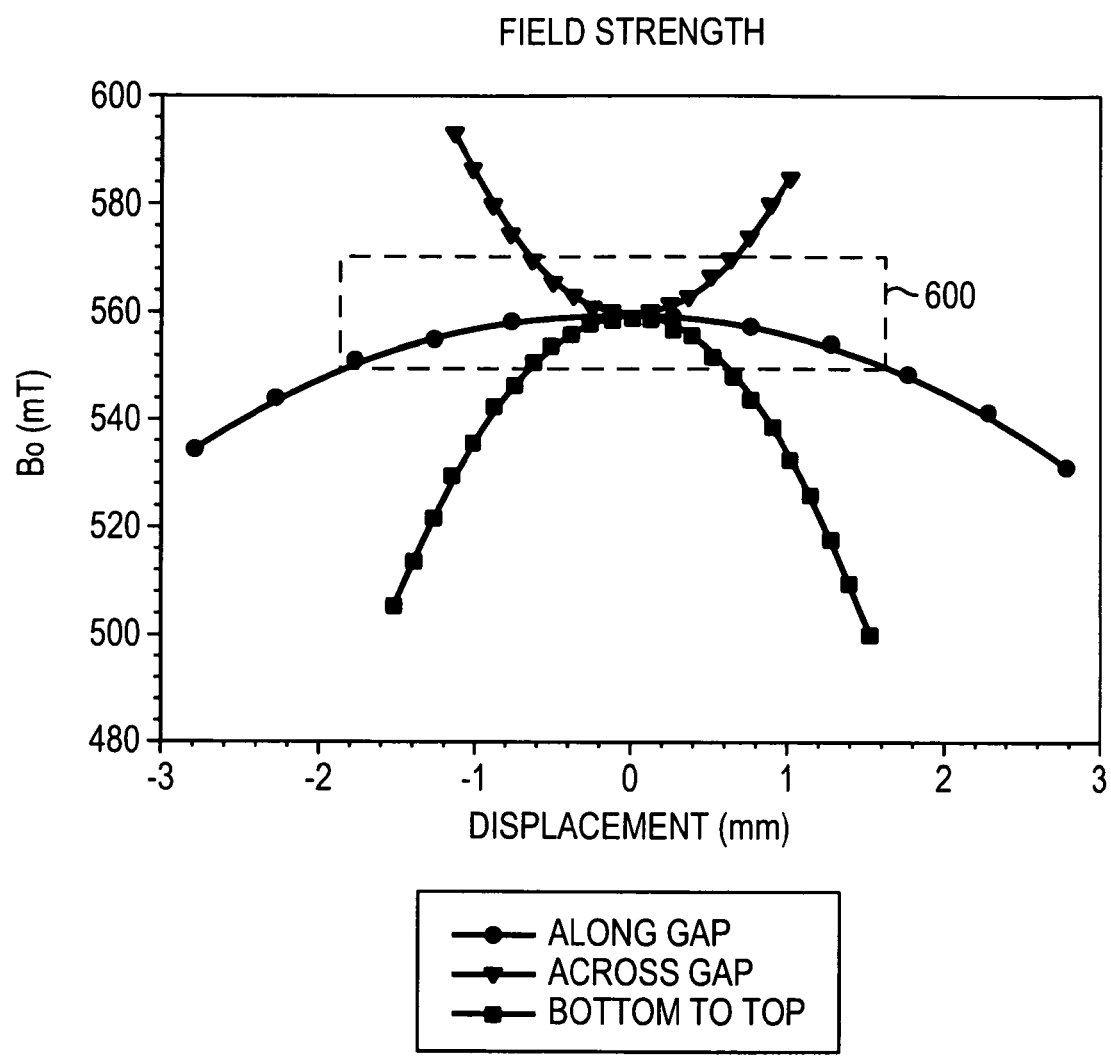
FIG. 6 shows the measured dependency of the magnetic field strength along three directions (along the gap, across the gap, and from bottom to top) within the gap between the magnets of the probehead shown in FIG. 2.
Figure 7:
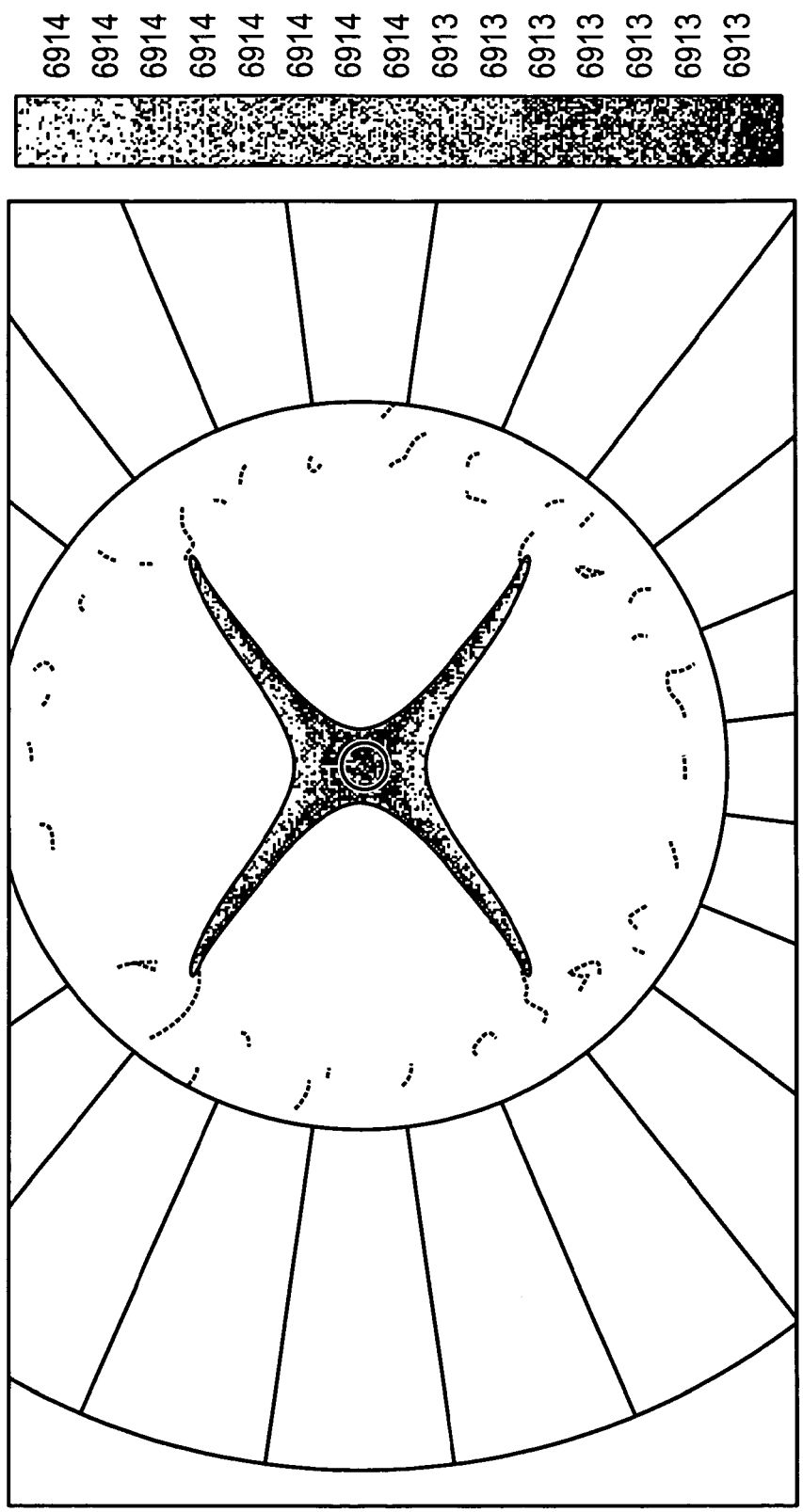
FIG. 7 provides a shaded field map within the center gap of a theoretical model magnet.

The magnetic field was mapped by measuring along the three axis around the geometrical center of the gap between the magnet pieces. FIGS. 6 and 7 show the magnetic field distribution.

A solenoid radiofrequency coil 204 was designed and positioned based on the magnetic field map with the goal of maximizing the sensitive volume, (e.g., the overlap volume of excitable volume and detection volume to be excited by short duration RF pulses). This was achieved by winding the radiofrequency coil to enclose a volume determined by the bandwidth of the RF pulses, provided in FIG. 6 as box shaped area 600, that is, approximately 1 mm diameter by about 2 mm length. The radiofrequency coil was fabricated using these dimensions. In this manner, a coil taking up about 20% of the gap between the magnets with a microliter sensitive volume was achieved. It is contemplated that this concept can be further exploited by, e.g., using more than one block at each side of the magnet. This allows for higher control on the field distribution and therefore a further size reduction keeping the same sensitive volume.

Figure 8:
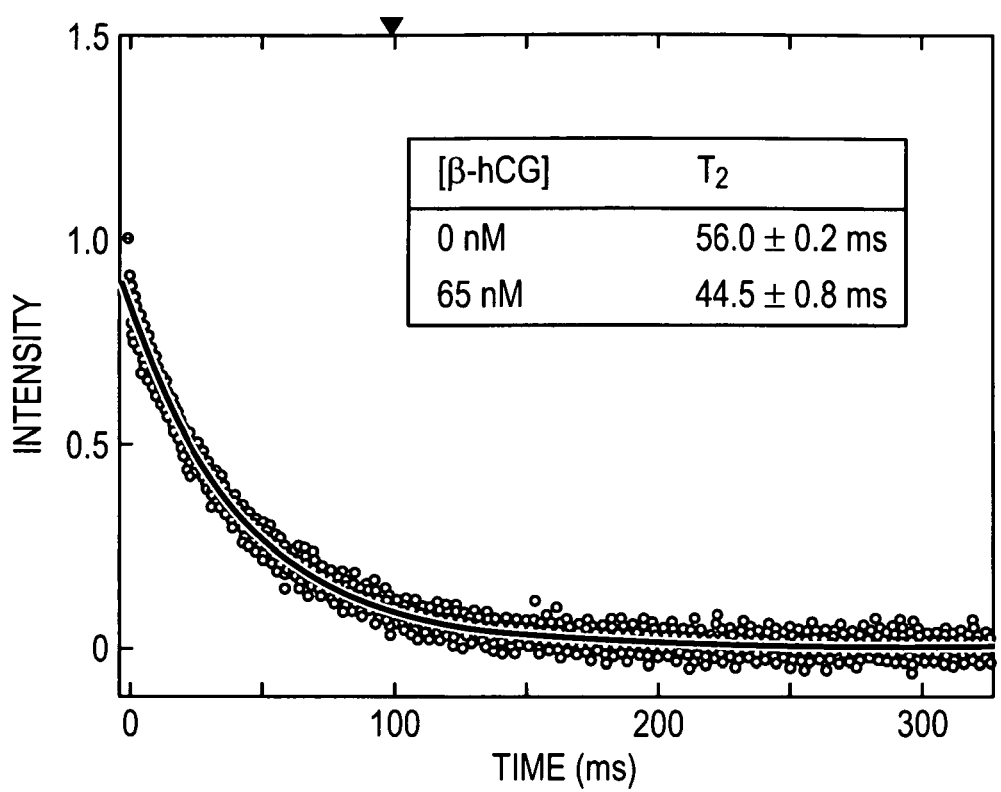
FIG. 8 provides a relaxation decay curve of a nanoparticle assay measured using the magnet and probehead in FIG. 2. A solution of magnetic relaxation switch nanoparticles sensitized to the protein β-hCG was used to detect a concentration of 65 nM (or 1 microgram/mL) hCG in 0.4 microliters of pH 7.4 PBS buffer.

The Abe probehead was attached to a KEA spectrometer (not shown; Magritek, Wellington, New Zeeland) outfitted with a Tomco pulse amplifier and controlled by Prospa softare (Magritek, Wellington, New Zeeland). The resonant circuit was tuned at the so-called Larmor frequency by using the "wobble" macro provided by the Prospa software, that is, using standard procedures known in the art and signal was acquired utilizing a conventional CPMG pulse sequence as controlled by the "cpmgadd" and "cpmgint" macros of the Prospa software, that is, by using standard procedures known in the art. FIG. 8 shows the signal decay utilizing a conventional CPMG pulse sequence.

The sample was loaded by means of a syringe outfitted with a fused silica glass capillary. A series of $CuSO_4$ samples were analyzed as well as nanoparticle assay solutions. The nanoparticle assay solutions consisted of antibody functionalized nanoparticles that bind to the beta subunit of the hCG protein (Kim, G. Y., Josephson, L., Langer, R., Cima, M. J. "Magnetic Relaxation Switch Detection of Human Chorionic Gonadotrophin". 2007, *Bioconjugate Chemistry* 18(6), 2024-2028.). Two solutions were prepared that contained 0.14 mM nanoparticle iron and 0 and 1 μg/mL beta subunit of hCG in PBS pH 7.4 buffer. The $T_2$ values of these solutions were measured in a volume of 300 μL on a Brukker minispec and in a volume of 0.4 μL on the Abe probehead. Both measurements showed a decrease in $T_2$ upon addition of hCG. However, the absolute $T_2$ values on the Abe magnet were lower than those for the Bruker minispec. It is believed that the reason for lower values is that the $T_2$ value measured with the Abe probehead is an effective $T_2$ value that includes effects from diffusion, temperature, and stimulated echoes. However, the most important result is that addition of hCG leads to a change in the measured $T_2$ and this information is successfully provided using the many orders of magnitude less expensive and smaller Abe probehead.

Example 2

Magnet configuration and yoke design can be accomplished initially by a theoretical prediction of what magnet and yoke configuration will lead to in terms of magnetic field strength. This was done by using standard analytical methods. A magnet assembly including two NdFeB permanent magnets (1"×1"×0.5") 301 was fabricated according to this method (see "T2-yoke" in FIG. 3). The yoke 300 was fabricated from steel stock using standard machining methods. The magnetic field in the x, y, and z directions was determined by fixing a gaussmeter probe relative to the magnet and moving the magnet in incremental steps with a three axis stage while recording the field strength as a function of position. The strength along the x, y, and z axes was measured by fixing two of the three directions to zero while incrementing the other. The same process was conducted for a pre-fabricated Halbach magnet (FIG. 4; the figure shows the Halbach magnet 400 while the magnetic field is being measured with a Gaussmeter probe 401).

Figure 9:
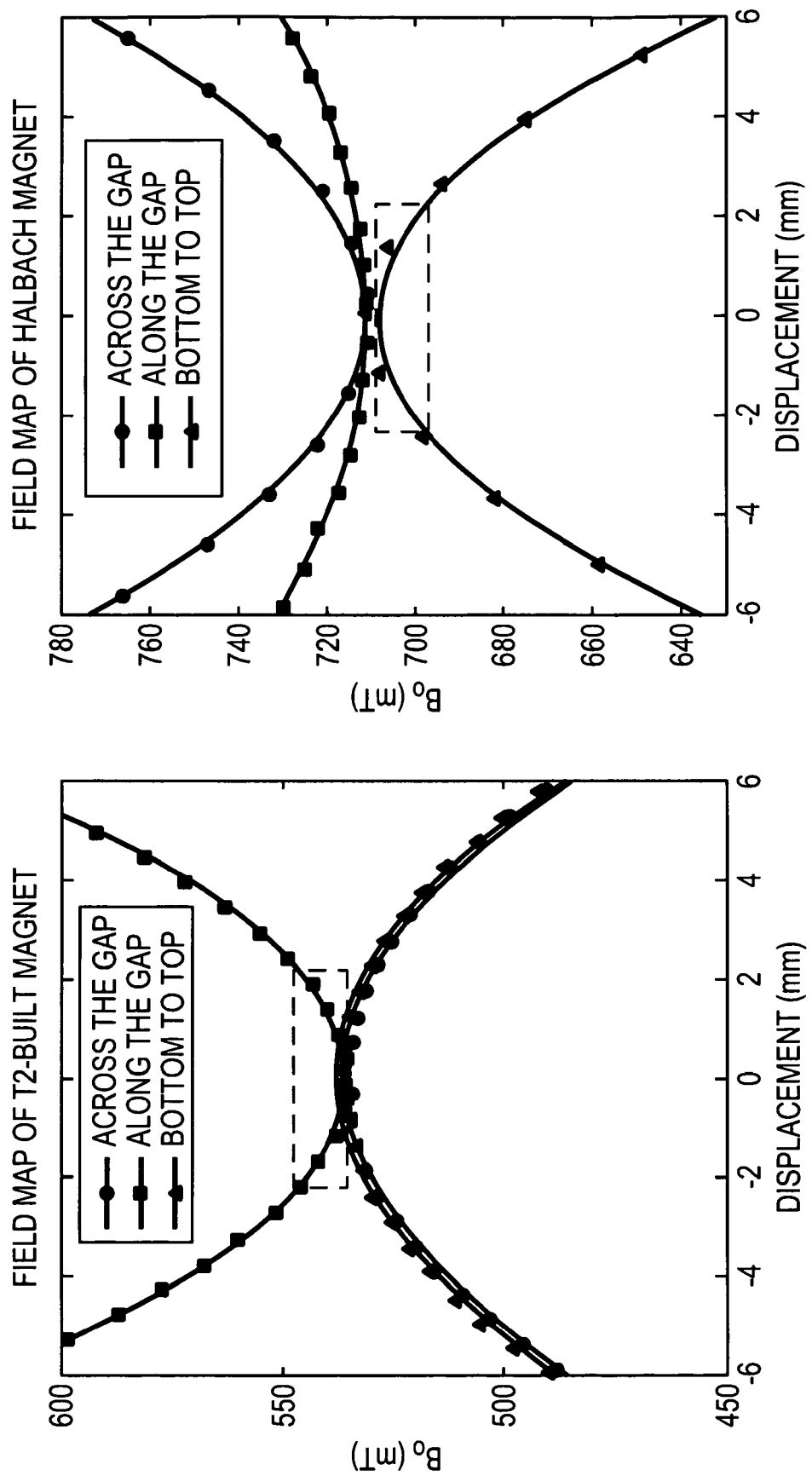
FIG. 9 shows the measured dependency of the magnetic field strength along three directions (along the gap, across the gap, and from bottom to top) within the gap between the magnets or within the center gap of the T2-yoke magnet (shown in FIG. 3) and the Halbach magnet (shown in FIG. 4) respectively. Examples of determining the region that can be excited for each dimension are shown with the dashed-line boxes.

Values obtained for a field map of each of the T2-yoke and the Halbach magnet configurations were plotted as function of position and magnetic field strength as shown in FIG. 9. Data were fitted with a quadratic function ($y=ax^2+bx+c$). The information of these plots was used to design a radiofrequency coil by determining what length in each dimension corresponds to a region that can be excited by a 2 μs RF pulse. For example, a 2 μs pulse excites a bandwidth of 500 kHz (bandwidth=(pulselength)$^{-1}$). For the T2-yoke shown in FIG. 3, the homogeneous region has a field strength of 535 militesla. The resonant frequency of hydrogen nuclei at this field can be calculated from $$f=\gamma B_o/2\pi \quad (1)$$

where f is the resonant frequency in Hz, γ the gyromagnetic ratio for $^1H$ nuclei (267.522×10$^6$ rad s$^{-1}$ T$^{-1}$), and $B_o$ the magnetic field in Tesla. Accordingly, the resonant frequency for the T2-yoke is 22.8 MHz. Equation 1 can also be used to determine the range of magnetic field over which a sample can be excited. Solving for $B_o$ and substituting 500 kHz for f, a $\Delta B_o$ of 11 millitesla is calculated. This value was used to determine the length in each dimension for the volume of sample that can be excited by a 2 μs pulse. FIG. 9 shows a graphical representation as to how this can be determined for each magnet. A box with a height corresponding to 11 mT is positioned on the plot such that one edge is at the minimum of the curve fit for "along the gap" and the other edge is used to determine the appropriate width of the box such that the two corners are traversed by the curve fit. The width of this box (~5 mm) corresponds to the length in this dimension that an excitation coil would enclose to maximize the sensitive volume. A similar box is shown for the Halbach magnet for the "bottom to top" dimension. Other analytical methods can be used to determine this, but the general idea is taking the $\Delta B_o$ and using the field map to translate that into a distance for each dimension.

Figure 10:
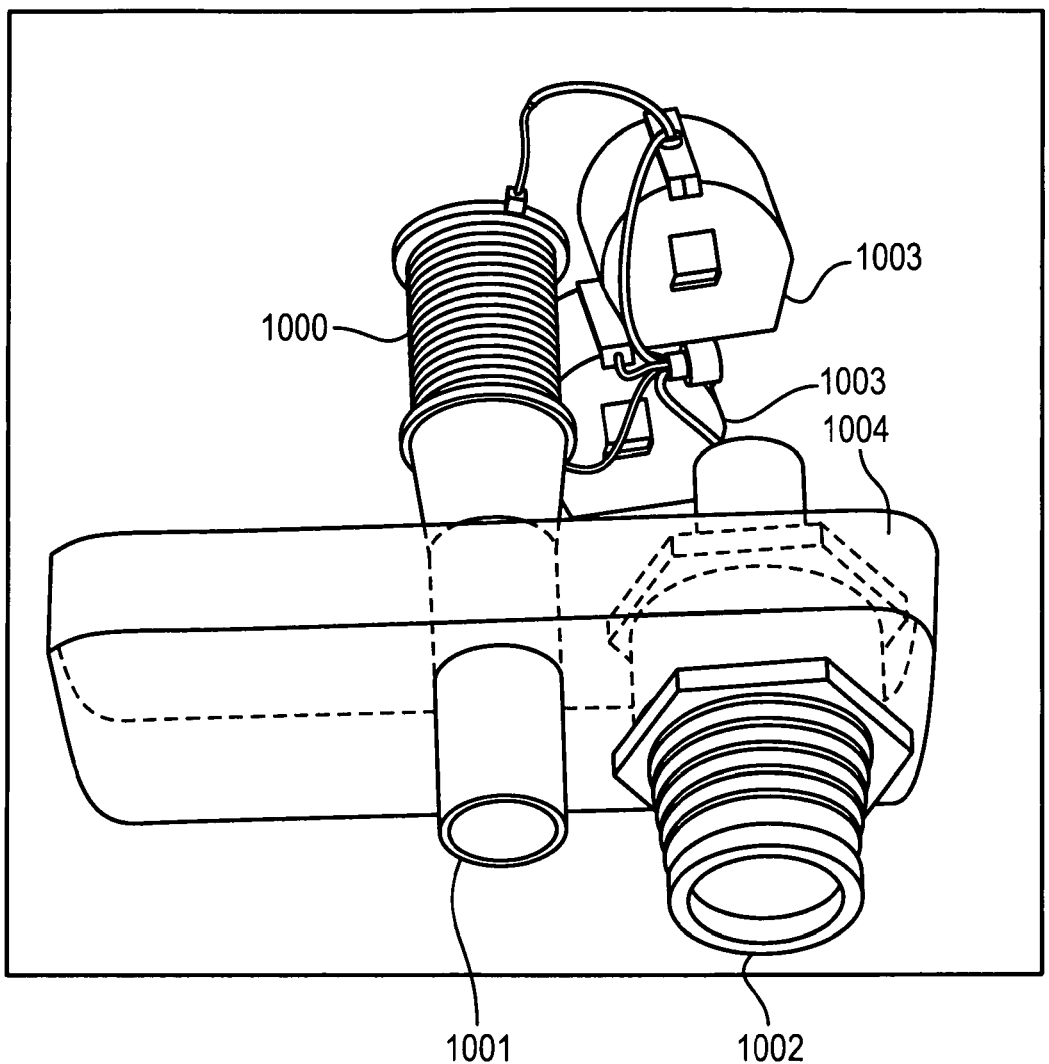
FIG. 10 shows the radiofrequency coil resonant circuit for the Halbach magnet.
Figure 11:
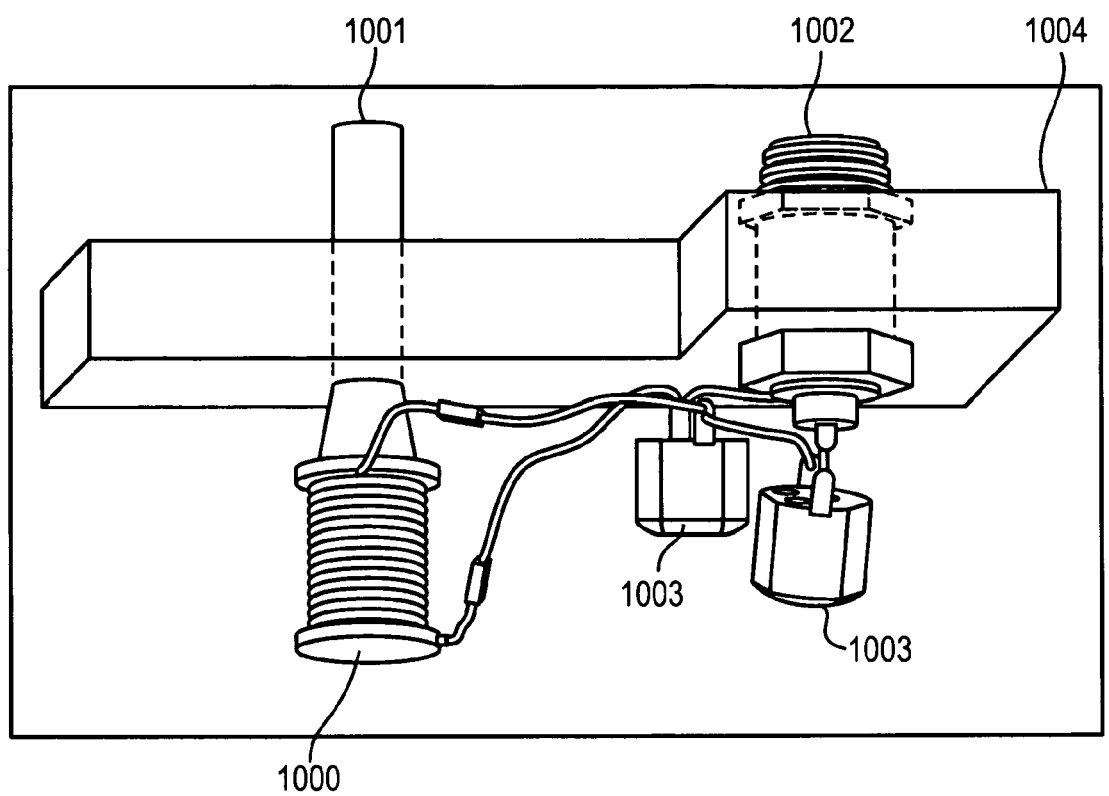
FIG. 11 shows the radiofrequency coil resonant circuit for the T2-yoke.

FIGS. 10 and 11 show radiofrequency circuits that were fabricated for the Halbach magnet and the T2-yoke respectively to form a complete probehead. The coils 1000 were custom made from inductors that are commercially available (inductors can be hand wound as for the previous example), enclose a sample volume to which sample can be delivered through a sample tube 1001, are part of a radiofrequency circuit that includes capacitors 1003 and a bulkhead SMA connector 1002, and are supported by a support plate 1004. Magnetic resonance signal was successfully measured using these probeheads (data not shown).

What is claimed is:

1. A probehead for use in a portable magnetic resonance relaxometer, comprising:
    (a) two permanent magnets connected by a steel c-shaped yoke, the south pole surface of one of the permanent magnets opposing the north pole surface of the other permanent magnet to form a gap and to provide the magnetic field in the gap at a strength of less than 1.1 Tesla;
    (b) a space capable of accommodating a sample volume having an associated excitable volume; and
    (c) a radiofrequency coil positioned partly or completely within the gap, said radiofrequency coil wound in a cylindrical shape to enclose a volume having a diameter of approximately 1 mm and a length of approximately 2 mm, the radiofrequency coil being positioned such that its detection volume overlaps at least partly with the excitable volume;
    wherein the magnetic field provided is inhomogeneous and the space accommodating the sample volume and the radiofrequency coil are adapted and positioned according to a radiofrequency CPMG pulse bandwidth optimized for a magnetic field distribution corresponding to the position of the sample volume; and wherein the probehead is optimized to obtain T2 relaxometry parameters from a sample contained in the detection volume.

2. The probehead of claim 1, a radiofrequency pulse being provided by the radiofrequency coil.

3. The probehead of claim 1, further comprising a housing, wherein the at least one magnet or magnetic field generator and the radiofrequency coil is attached to the housing.

4. The probehead of claim 1, wherein the detection volume includes between about 10 percent and about 100 percent of the excitable volume.

5. The probehead of claim 1, wherein (i) the radiofrequency coil is part of a radiofrequency circuit, the radiofrequency circuit comprising a capacitor and (ii) the radiofrequency coil is positioned to have the coil volume include between about 80 percent and about 100% of the excitable volume.

6. The probehead of claim 1, wherein the radiofrequency pulse length is between about 0.4 microseconds and about 10 microseconds.

7. The probehead of claim 1, further comprising at least one capacitor, the at least one capacitor and the radiofrequency coil being part of a radiofrequency circuit.

8. The probehead of claim 1, wherein each of the at least one magnet or magnetic field generator is in any dimension less than about two inches.

9. The probehead of claim 1, wherein said sample volume comprises a sensing agent capable of sensing a sample characteristic.

10. The probehead of claim 9, wherein said sensing agent comprises dry reagents compositions, magnetic particles, responsive polymers, or magnetic resonance contrast agents.

11. The probehead of claim 9, wherein said sample characteristic is hydration state.

12. The probehead of claim 9, wherein said sensing agent is a superparamagnetic nanoparticle.

13. The probehead of claim 12, wherein said superparamagnetic nanoparticles have binding moieties attached such that binding of said nanoparticles to an analyte results in an alteration of T2 signal.

14. A method of preparing a probehead for use in a portable magnetic resonance relaxometer, the method comprising the steps of:
    (a) attaching two magnets or two magnetic field generators to a steel c-shaped yoke such that the south pole surface of one of the magnets or magnetic field generators opposes the north pole surface of the other magnet or magnetic field generator to form a gap between the magnets or magnetic field generators and to provide a magnetic field in the gap having a strength of less than about 1.1 Tesla;
    (b) positioning a space capable of accommodating a sample volume having an associated excitable volume; and
    (c) positioning a radiofrequency coil wound in a cylindrical shape to enclose a volume having a diameter of approximately 1 mm and a length of approximately 2 mm and being adapted to emit a radiofrequency pulse with a pulse length, the radiofrequency coil being positioned and designed to have the detection volume at least partly overlap with an excitable volume within the gap;
    wherein the probehead is optimized to obtain T2 relaxometry parameters from a sample contained in the sample volume.

* * * * *